US009708255B2

(12) United States Patent
Casero et al.

(10) Patent No.: US 9,708,255 B2
(45) Date of Patent: Jul. 18, 2017

(54) (BIS)UREA AND (BIS)THIOUREA COMPOUNDS AS EPIGENIC MODULATORS OF LYSINE-SPECIFIC DEMETHYLASE 1 AND METHODS OF TREATING DISORDERS

(75) Inventors: Robert A. Casero, Glen Arm, MD (US); Patrick M. Woster, Canton, MI (US)

(73) Assignees: Robert A. Casero, Glen Arm, MD (US); Patrick M. Woster, Charleston, SC (US)

( * ) Notice: Subject to any disclaimer, the term of this patent is extended or adjusted under 35 U.S.C. 154(b) by 818 days.

(21) Appl. No.: 13/391,247

(22) PCT Filed: Aug. 18, 2010

(86) PCT No.: PCT/US2010/045903
§ 371 (c)(1),
(2), (4) Date: Sep. 4, 2012

(87) PCT Pub. No.: WO2011/022489
PCT Pub. Date: Feb. 24, 2011

(65) Prior Publication Data
US 2012/0322877 A1 Dec. 20, 2012

Related U.S. Application Data

(60) Provisional application No. 61/234,799, filed on Aug. 18, 2009.

(51) Int. Cl.
*C07C 275/00* (2006.01)
*C07C 335/00* (2006.01)
*A61K 31/17* (2006.01)
*C07C 335/08* (2006.01)
*A61K 31/155* (2006.01)
*A61K 45/06* (2006.01)
*C07C 275/14* (2006.01)
*C07C 275/24* (2006.01)
*C07C 275/28* (2006.01)
*C07C 335/12* (2006.01)

(52) U.S. Cl.
CPC .......... *C07C 335/08* (2013.01); *A61K 31/155* (2013.01); *A61K 31/17* (2013.01); *A61K 45/06* (2013.01); *C07C 275/14* (2013.01); *C07C 275/24* (2013.01); *C07C 275/28* (2013.01); *C07C 335/12* (2013.01)

(58) Field of Classification Search
CPC .... A61K 31/17; C07C 275/14; C07C 275/24; C07C 275/28; C07C 335/08; C07C 335/14; C07C 279/26
See application file for complete search history.

(56) References Cited

U.S. PATENT DOCUMENTS

| 4,486,391 A | 12/1984 | Hashimoto |
| 2009/0182019 A1 | 7/2009 | Casero et al. |
| 2010/0273745 A1 | 10/2010 | Woster et al. |
| 2011/0092601 A1 | 4/2011 | Woster et al. |

FOREIGN PATENT DOCUMENTS

| DE | 1150045 | * 6/1963 |
| WO | WO-2007/021839 A2 | 2/2007 |

OTHER PUBLICATIONS

Golding et al., Journal of Chemical Research, Synopses (1981), (11), 342.*
S. Smarma et al., "(Bis)urea and (Bis)thiourea Inhibitors of Lysine-Specific Demethylase 1 as Epigenetic Modulators"; J. Med Chem. vol. 53, pp. 5197-5212 (2010).
S. Uchida et al., "Properties of dendritic and cyclic thiourea derivatives as neutral carriers for anion sensors", vol. 53, No. 9, pp. 943-952 (2004).
S. Soomro et al, "Dendrimers with peripheral stilbene chromophores", Institute of Organic Chemistry, pp. 8089 (2006).
R. Chen, "Noncovalent Anchoring of Homogeneous Catalysts to Silica Supports with Well-Defined Binding Sites", American Chemical Society, pp. 14557-14566 (2004).
"Written Opinion of the International Searching Authority", from corresponding PCT Application No. PCT/US2010/045903, mailed Apr. 25, 2011.
R. Chen et al., "Noncovalent Anchoring of Homogeneous Catalysts to Silica Supports with Well-Defined Binding Sites", J. Am. Chem. Soc., vol. 126, pp. 14557-14566 (2004).
S.A. Soomro et al., "Dendrimers with peripheral stilbene chromophores", Tetrahedron, vol. 62, pp. 8089-8094 (2006).
Bi, X. et al., "Novel alkylpolyaminoguanidines and alkylpolyaminobiguanides with potent antitrypanosomal activity," Bioorg. Med. Chem. Litt., vol. 16(23) 2006:3229-3232.
Casero, Robert A. Jr. et al., "Recent Advances in the Development of Polyamine Analogues as Antitumor Agents," J. Med. Chem., vol. 52(15) 2009:4551-4573.
Dudley, Harold Ward et al., "The Chemical Constitution of Spermine. I. The Isolation of Spermine from Animal Tissues, and the Preparation of Its Salts," Biochem. J., vol. 18(6) 1924:1263-1272.
Huang, Yi et al., "Inhibition of lysine-specific demethylase 1 by polyamine analogues resuts in reexpression of aberrantly silenced genes," PNAS, vol. 104(19) 2007:8023-8028.
Schlogl, K. et al., "Uber Bis-trimethoxy-benzamide, -phenylharnstoffe, -phenylurethane and verwandte Derivate von Dialkyl-athylendiaminen und -piperazinen," Monatshefte fur Chemie, vol. 95(3) 1964:942-949.
Woster, Patrick M. et al., "Report: Lysine-Specific Demethylase 1 Drug Discovery Program," 10 pages (2009).
Supplementary European Search Report for Application No. 10810552.9, 6 pages, dated Dec. 12, 2012.

* cited by examiner

*Primary Examiner* — Shoba Kantamneni
(74) *Attorney, Agent, or Firm* — Burns & Levinson, LLP; Daniel W. Clarke

(57) ABSTRACT

The invention provides for novel (bis)urea and (bis)thiourea compounds which are inhibitors of lysine-specific demethylase 1 (LSD1). Such compounds may be used to treat disorders, including cancer.

8 Claims, 4 Drawing Sheets

A

SFRP2

B

GATA4

(BIS)UREA AND (BIS)THIOUREA COMPOUNDS AS EPIGENIC MODULATORS OF LYSINE-SPECIFIC DEMETHYLASE 1 AND METHODS OF TREATING DISORDERS

RELATED APPLICATIONS

This application is a US National stage application of PCT/US2010/045902 (WO2011/022489), filed on Aug. 19, 2010, which claims priority to U.S. Ser. No. 61/234,799, filed on Aug. 18, 2009. The entire contents of the above-referenced applications are incorporated herein by reference.

TECHNICAL FIELD

The invention provides for novel (bis)urea and (bis) thiourea compounds which are inhibitors of lysine-specific demethylase 1 (LSD1). Such compounds may be used to treat disorders, including cancer.

BACKGROUND OF THE INVENTION

Chromatin architecture is a key determinant in the regulation of gene expression, and this architecture is strongly influenced by post-translational modifications of histones (Marks, P. A.; et al. *Curr Opin Oncol* 2001, 13 (6), 477-483; Luger, K.; et al. *Nature* 1997, 389 (6648), 251-260). Histone protein tails contain lysine residues that interact with the negative charges on the DNA backbone. These lysine-containing tails, consisting of up to 40 amino acid residues, protrude through the DNA strand, and act as a site for post-translational modification of chromatin, allowing alteration of higher order nucleosome structure (Jenuwein, T.; Allis, C. D. *Science* 2001, 293 (5532), 1074-1080). Multiple post-translational modifications of histones can mediate epigenetic remodeling of chromatin, with acetylation being the best characterized process (Johnstone, R. W. *Nat Rev Drug Discov* 2002, 1 (4), 287-299). Transcriptional repression is associated with specific CpG island DNA methylation and recruitment of histone deacetylases (HDACs) to gene promoters that cooperate in the epigenetic silencing of specific genes (Herman, J. G.; Baylin, S. B. *N Engl J Med* 2003, 349 (21), 2042-2054; Robertson, K. D. *Oncogene* 2001, 20 (24), 3139-3155). Normal mammalian cells exhibit an exquisite level of control of chromatin architecture by maintaining a balance between histone acetyltransferase (HAT) and HDAC activity (Shogren-Knaak, M.; et al. *Science* 2006, 311 (5762), 844-847).

In cancer, CpG island DNA promoter hypermethylation in combination with other chromatin modifications, including decreased activating marks and increased repressive marks on histone proteins 3 and 4, have been associated with the silencing of tumor suppressor genes (Baylin, S. B.; Ohm, J. E. *Nat Rev Cancer* 2006, 6 (2), 107-116). The important role of promoter CpG island methylation and its relationship to covalent histone modifications has recently been reviewed (Jones, P. A.; Baylin, S. B. *Cell* 2007, 128 (4), 683-692). As was mentioned above, the N-terminal lysine tails of histones can undergo numerous posttranslational modifications, including phosphorylation, ubiquitination, acetylation and methylation (Johnstone, R. W. *Nat Rev Drug Discov* 2002, 1 (4), 287-299; Shi, Y.; et al. *Cell* 2004, 119 (7), 941-953; Whetstine, J. R.; et al. *Cell* 2006, 125 (3), 467-481). To date, 17 lysine residues and 7 arginine residues on histone proteins have been shown to undergo methylation, and lysine methylation on histones can signal transcriptional activation or repression, depending on the specific lysine residue involved (Bannister, A. J.; et al. *Nature* 2005, 436 (7054), 1103-1106; Kouzarides, T. *Curr Opin Genet Dev* 2002, 12 (2), 198-209; Martin, C.; et al. *Nat Rev Mol Cell Biol* 2005, 6 (11), 838-849; Zhang, Y.; Reinberg, D. *Genes Dev* 2001, 15 (18), 2343-2360). All known histone lysine methyltransferases contain a conserved SET methyltransferase domain, and it has been shown that aberrant methylation of histones due to SET domain deregulation is linked to carcinogenesis (Schneider, R.; et al. *Trends Biochem Sci* 2002, 27 (8), 396-402). Histone methylation, once thought to be an irreversible process, has recently been shown to be a dynamic process regulated by the addition of methyl groups by histone methyltransferases and removal of methyl groups from mono- and dimethyllysines by lysine specific demethylase 1 (LSD1), and from mono-, di, and trimethyllysines by specific Jumonji C (JmjC) domain-containing demethylases (Shi, Y.; et al. *Cell* 2004, 119 (7), 941-953; Whetstine, J. R.; et al. *Cell* 2006, 125 (3), 467-481; Tsukada, Y.; Zhang, Y. *Methods* 2006, 40 (4), 318-326; Huarte, M.; et al. *J Biol Chem* 2007). Additional demethylases in the JmjC demethylase class are continuing to be identified (Liang, G.; et al. *Nat Struct Mol Biol* 2007, 14 (3), 243-245; Secombe, J.; et al. *Genes Dev* 2007, 21 (5), 537-551. Recent evidence suggests that LSD1 is required for maintenance of global DNA methylation, indicating that the LSD1-mediated demethylation is a general mechanism for transcriptional control (Wang, J.; et al. *Nat Genet.* 2009, 41 (1), 125-129).

A key positive chromatin mark found associated with promoters of active genes is histone 3 dimethyllysine 4 (H3K4me2) (Liang, G., et al. *Proc Natl Acad Sci USA* 2004, 101 (19), 7357-7362; Schneider, R.; et al. *Nat Cell Biol* 2004, 6 (1), 73-77). LSD1, also known as BHC110 and KDM1, catalyzes the oxidative demethylation of histone 3 methyllysine 4 (H3K4me1) and H3K4me2, and is associated with transcriptional repression. H3K4me2 is a transcription-activating chromatin mark at gene promoters, and demethylation of this mark by LSD1 may prevent expression of tumor suppressor genes important in human cancer (Huang, Y.; et al. *Proc Natl Acad Sci USA* 2007, 104 (19), 8023-8028). Thus, LSD1 is emerging as an important new target for the development of specific inhibitors as a new class of antitumor drugs (Stavropoulos, P.; Hoelz, A. *Expert Opin Ther Targets* 2007, 11 (6), 809-820).

To date, only a few existing compounds have been shown to act as inhibitors of LSD1. The active site structure of LSD1 has considerable sequence homology to monoamine oxidases A and B (MAO A and B), and to $N^1$-acetylpolyamine oxidase (APAO) and spermine oxidase (SMO) (Shi, Y.; et al. *Cell* 2004, 119 (7), 941-953; Lee, M. G.; et al. *Chem Biol* 2006, 13 (6), 563-567; Schmidt, D. M.; McCafferty, D. G. *Biochemistry* 2007, 46 (14), 4408-4416). It has been shown that classical MAO inhibitors phenelzine and tranylcypromine inactivate nucleosomal demethylation by the recombinant LSD1/CoRest complex, and increase global levels of H3K4me2 in the P19 cell line. The synthetic substrate analogue aziridinyl-K4H3$_{1-21}$ reversibly inhibited LSD1 with an IC$_{50}$ of 15.6 µM, while propargyl-K4H3$_{1-21}$ produced time-dependent inactivation with a K$_i$ of 16.6 µM (Culhane, J. C.; et al. *J Am Chem Soc* 2006, 128 (14), 4536-4537). Propargyl-K4H3$_{1-21}$ was later shown to inactivate LSD1 through formation of a covalent adduct with the enzyme-bound flavin cofactor (Schmidt, D. M.; McCafferty, D. G. *Biochemistry* 2007, 46 (14), 4408-4416; Szewczuk, L. M.; et al. *Biochemistry* 2007, 46, 6892-6902). McCafferty et al. recently described the synthesis of a series of trans-2-arylcyclopropylamine analogues that inhibit LSD1 with K, values between 188 and 566 µM (Gooden, D. M.; et al.

*Bioorg Med Chem Lett* 2008, 18 (10), 3047-3051). However, in all but one instance, these analogues were 1-2 orders of magnitude more potent against MAO A and MOA B. Most recently, Ueda and coworkers identified small molecule tranylcypromine derivatives that are selective for LSD1 over MAO-A and MAO-B, and Binda et al. described similar tranylcypromine analogues that exhibited partial selectivity between LSD1 and the newly identified histone demethylase LSD2 (Ueda, R.; et al. *J Am Chem Soc* 2009, 131 (48), 17536-17537; Binda, C.; et al. *J Am Chem Soc* 2010, 132, ePub 10.1021/ja101557k).

LSD1 was identified in part because its C-terminal domain shares significant sequence homology with the amine oxidases acetylpolyamine oxidase (APAO) and spermine oxidase (SMO) (Wang, Y.; et al. *Biochem Biophys Res Commun* 2003, 304 (4), 605-611). Several groups have identified amines, guanidines or similar analogues that act as selective modulators of these 2 amine oxidases (Wang, Y.; et al. *Biochem Biophys Res Commun* 2003, 304 (4), 605-611; Ferioli, M. E.; et al. *Toxicol Appl Pharmacol* 2004, 201 (2), 105-111; Casara, P.; et al. *Tet. Letters* 1984, 25, 1891-1894; Bellelli, A.; et al. *Biochem Biophys Res Commun* 2004, 322 (1), 1-8; Wang, Y.; et al. *Cancer Chemother Pharmacol* 2005, 56 (1), 83-90; Cona, A.; et al. *Biochemistry* 2004, 43 (12), 3426-3435; Stranska, J.; et al. *Biochimie* 2007, 89 (1), 135-144). We previously reported the synthesis of a novel series of (bis)guanidines and (bis)biguanides that are potent antitrypanosomal agents in vitro, with $IC_{50}$ values against *Trypanosoma brucei* as low as 90 nM (Bi, X.; et al. *Bioorg Med Chem Lett* 2006, 16 (12), 3229-3232).

Because of the promising cellular effects of various (bis)guanidines and (bis)biguanides the synthesis and evaluation of additional analogues was undertaken.

SUMMARY OF THE INVENTION

In one aspect, the invention provides a compound of Formula I or Formula II:

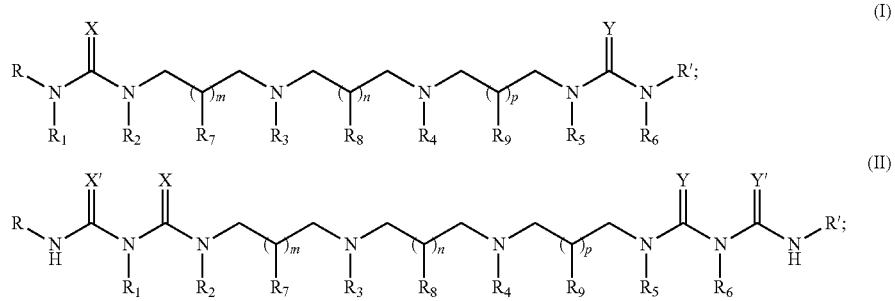

and salts, solvates and hydrates thereof, wherein,
each X is independently O or S;
each Y is independently NR", O or S;
X' is O or S;
Y' is NR", O or S;
each R is independently H, —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; —$C_3$-$C_{12}$ cycloalkyl, —$C_3$-$C_{12}$ heterocycloalkyl, —$C_6$-$C_{20}$ aralkyl, —$C_3$-$C_{12}$ aryl, —$C_3$-$C_{12}$ heteroaryl, $OR_A$, $SR_A$, and $NR_AR_A$; each of which is optionally substituted;
each R' is independently H, —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; —$C_3$-$C_{12}$ cycloalkyl, —$C_3$-$C_{12}$ heterocycloalkyl, —$C_6$-$C_{20}$ aralkyl, —$C_3$-$C_{12}$ aryl, —$C_3$-$C_{12}$ heteroaryl, $OR_A$, $SR_A$, and $NR_AR_A$; each of which is optionally substituted;
each R" is independently H, optionally substituted alkyl, optionally substituted aralkyl, or optionally substituted aryl;
each of $R_1$, $R_2$, $R_3$, $R_4$, $R_5$, and $R_6$ are independently selected from H, alkyl, aralkyl, haloalkyl, aryl, heteroaryl, and heteroaralkyl, each of which is optionally substituted;
each of $R_7$, $R_8$, and $R_9$ are independently selected from H, —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; —$C_3$-$C_{12}$ cycloalkyl, —$C_3$-$C_{12}$ heterocycloalkyl, —$C_6$-$C_{20}$ aralkyl, —$C_3$-$C_{12}$ aryl, —$C_3$-$C_{12}$ heteroaryl, $OR_A$, $SR_A$, and $NR_AR_A$; each of which is optionally substituted;
each $R_A$ is independently selected from H, alkyl, aralkyl, aryl, or heteroaryl, each of which is optionally substituted;
m is 1, 2, or 3;
n is 1, 2, 3, 4, 5, 6, 7, 8, 9, or 10; and
p is 1, 2, or 3.

In another aspect, the invention provides a pharmaceutical composition comprising a therapeutically effective amount of a compound of formula I or formula II, or a pharmaceutically acceptable salt, solvate or hydrate thereof, in combination with a pharmaceutically acceptable carrier or excipient.

In certain aspects, the invention provides a method of treating a disease or disorder associated with lysine-specific demethylase 1 (LSD1) in a subject, the method comprising the step of administering to the subject an effective amount of a compound of formula I or formula II, or a pharmaceutically acceptable salt, ester or hydrate thereof.

In another aspect, the invention provides a method of treating a disease or disorder associated with lysine-specific demethylase 1 (LSD1) in a subject, wherein the subject is identified as being in need of a LSD1 inhibitor, the method comprising the step of administering to the subject an effective amount of a compound of formula I or formula II, or a pharmaceutically acceptable salt, ester or hydrate thereof.

In another aspect, the invention provides a method of inhibiting or reducing lysine-specific demethylase 1 (LSD1) in a subject, the method comprising the step of administering to the subject an effective amount of a compound of formula I or formula II; wherein said compound is identified in a screening assay.

In another aspect, the invention provides a method of treating tumor, cancer, or neoplasia in a subject, the method comprising the step of administering to the subject an effective amount of a compound of formula I or formula II, or a pharmaceutically acceptable salt, solvate or hydrate thereof.

In another aspect, the invention provides a kit comprising an effective amount of a compound of formula I or formula II in unit dosage form, together with instructions for administering the compound to a subject suffering from or susceptible to a LSD1-related disease.

DETAILED DESCRIPTION OF THE INVENTION

Figure 1:
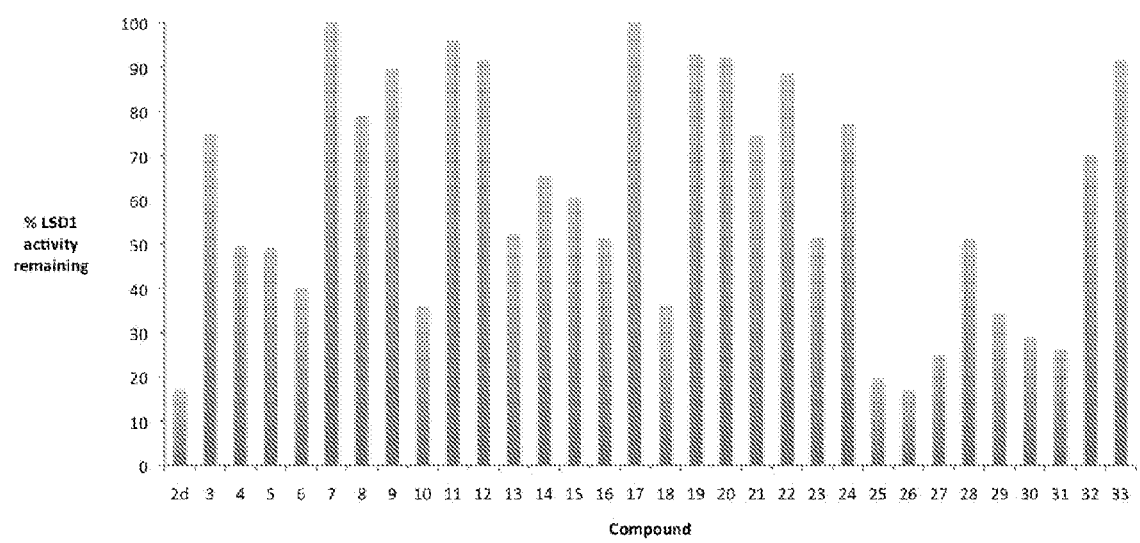
FIG. 1. Effect of compounds 3-33 on LSD1 activity in vitro. Percent of LSD1 activity remaining was determined following 24-hour treatment with 10 mM of each test compound as determined by the luminol-dependent chemiluminescence method.

In one aspect, the invention provides a compound of Formula I or Formula II:

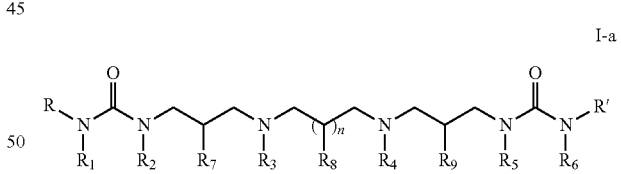

(I)

(II)

and salts, solvates and hydrates thereof, wherein,
each X is independently O or S;
each Y is independently NR", O or S;
X' is O or S;
Y' is NR", O or S;
each R is independently H, —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; —$C_3$-$C_{12}$ cycloalkyl, —$C_3$-$C_{12}$ heterocycloalkyl, —$C_6$-$C_{20}$ aralkyl, —$C_3$-$C_{12}$ aryl, —$C_3$-$C_{12}$ heteroaryl, $OR_A$, $SR_A$, and $NR_AR_A$; each of which is optionally substituted;
each R' is independently H, —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; —$C_3$-$C_{12}$ cycloalkyl, —$C_3$-$C_{12}$ heterocycloalkyl, —$C_6$-$C_{20}$ aralkyl, —$C_3$-$C_{12}$ aryl, —$C_3$-$C_{12}$ heteroaryl, $OR_A$, $SR_A$, and $NR_AR_A$; each of which is optionally substituted;
each R" is independently H, optionally substituted alkyl, optionally substituted aralkyl, or optionally substituted aryl;
each of $R_1$, $R_2$, $R_3$, $R_4$, $R_5$, and $R_6$ are independently selected from H, alkyl, aralkyl, haloalkyl, aryl, heteroaryl, and heteroaralkyl, each of which is optionally substituted;
each of $R_7$, $R_8$, and $R_9$ are independently selected from H, —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; —$C_3$-$C_{12}$ cycloalkyl, —$C_3$-$C_{12}$ heterocycloalkyl, —$C_6$-$C_{20}$ aralkyl, —$C_3$-$C_{12}$ aryl, —$C_3$-$C_{12}$ heteroaryl, $OR_A$, $SR_A$, and $NR_AR_A$; each of which is optionally substituted;
each $R_A$ is independently selected from H, alkyl, aralkyl, aryl, or heteroaryl, each of which is optionally substituted;
m is 1, 2, or 3;
n is 1, 2, 3, 4, 5, 6, 7, 8, 9, or 10; and
p is 1, 2, or 3.

In one embodiment, each R is independently H, —$C_1$-$C_8$ alkyl, —$C_6$-$C_{20}$ aralkyl, or —$C_3$-$C_{12}$ aryl; each of which is optionally substituted.

In another embodiment, each R' is independently H, —$C_1$-$C_8$ alkyl, —$C_6$-$C_{20}$ aralkyl, or —$C_3$-$C_{12}$ aryl; each of which is optionally substituted.

In certain embodiments, m and p are 1.

In a first embodiment, the invention provides a compound as described above,
wherein the compound is a compound of formula I-a, I-b, I-c, or I-d:

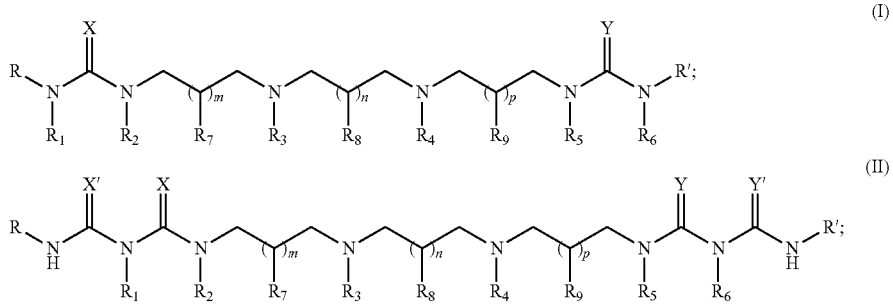

I-a

-continued

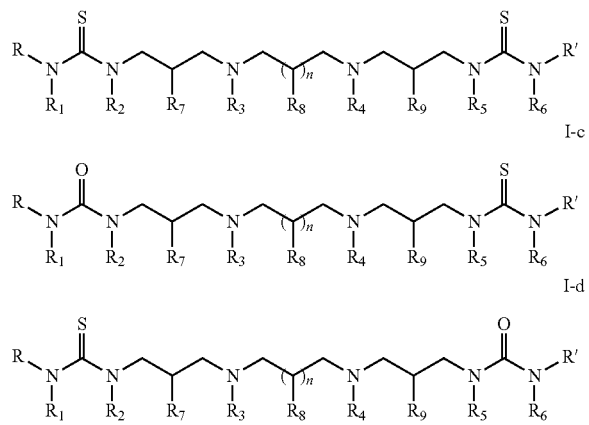

and salts, solvates and hydrates thereof, wherein, each R is independently H, —$C_1$-$C_8$ alkyl, —$C_6$-$C_{20}$ aralkyl, or —$C_3$-$C_{12}$ aryl; each of which is optionally substituted.

each R' is independently H, —$C_1$-$C_8$ alkyl, —$C_6$-$C_{20}$ aralkyl, or —$C_3$-$C_{12}$ aryl; each of which is optionally substituted.

each of $R_1$, $R_2$, $R_3$, $R_4$, $R_5$, and $R_6$ are independently selected from H, alkyl, aralkyl, haloalkyl, aryl, heteroaryl, and heteroaralkyl, each of which is optionally substituted;

each of $R_7$, $R_8$, and $R_9$ are independently selected from H, —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; —$C_3$-$C_{12}$ cycloalkyl, —$C_3$-$C_{12}$ heterocycloalkyl, —$C_6$-$C_{20}$ aralkyl, —$C_3$-$C_{12}$ aryl, —$C_3$-$C_{12}$ heteroaryl, $OR_A$, $SR_A$, and $NR_AR_A$; each of which is optionally substituted;

each $R_A$ is independently selected from H, alkyl, aralkyl, aryl, or heteroaryl, each of which is optionally substituted; and n is 1, 2, 3, 4, 5, 6, 7, 8, 9, or 10.

In various embodiments, each R is independently H, methyl, ethyl, propyl, i-propyl, butyl, s-butyl, t-butyl, pentyl, hexyl, heptyl, phenyl, benzyl, ethyl phenyl, propyl phenyl, or naphthyl, each of which is optionally substituted.

In a further embodiment, each R is independently H, methyl, ethyl, propyl, phenyl, benzyl, 3,3-diphenylpropyl, 2,2-diphenylethyl, or diphenylmethyl.

In another embodiment, each $R_1$, $R_2$, $R_3$, $R_4$, $R_5$, and $R_6$ are H.

In various embodiments, each $R_7$, $R_8$, and $R_9$ are H.

In other embodiments, each n is independently 1, 2, 3, 4, 5, or 6.

In a second embodiment, the invention provides a compound as described above, wherein the compound is a compound of formula II-a, II-b, II-c, or II-d:

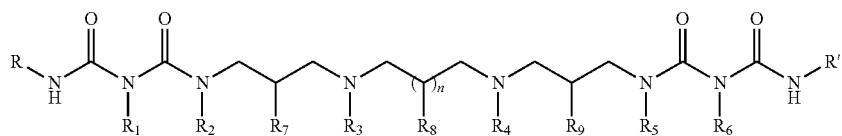

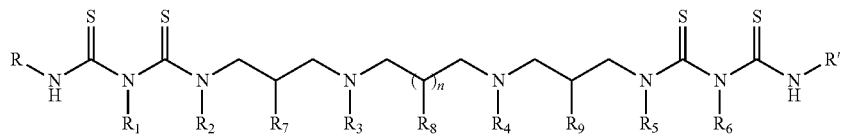

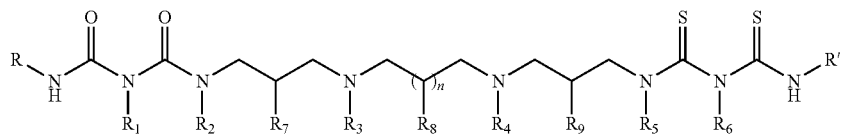

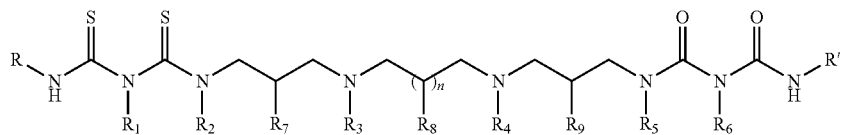

and salts, solvates and hydrates thereof, wherein, each R is independently H, —$C_1$-$C_8$ alkyl, —$C_6$-$C_{20}$ aralkyl, or —$C_3$-$C_{12}$ aryl; each of which is optionally substituted.

each R' is independently H, —C$_1$-C$_8$ alkyl, —C$_6$-C$_{20}$ aralkyl, or —C$_3$-C$_{12}$ aryl; each of which is optionally substituted.

each of R$_1$, R$_2$, R$_3$, R$_4$, R$_5$, and R$_6$ are independently selected from H, alkyl, aralkyl, haloalkyl, aryl, heteroaryl, and heteroaralkyl, each of which is optionally substituted;

each of R$_7$, R$_8$, and R$_9$ are independently selected from H, —C$_1$-C$_8$ alkyl, —C$_2$-C$_8$ alkenyl or —C$_2$-C$_8$ alkynyl, each containing 0, 1, 2, or 3 heteroatoms independently selected from O, S, and N; —C$_3$-C$_{12}$ cycloalkyl, —C$_3$-C$_{12}$ heterocycloalkyl, —C$_6$-C$_{20}$ aralkyl, —C$_3$-C$_{12}$ aryl, —C$_3$-C$_{12}$ heteroaryl, OR$_A$, SR$_A$, and NR$_A$R$_A$; each of which is optionally substituted;

each R$_A$ is independently selected from H, alkyl, aralkyl, aryl, or heteroaryl, each of which is optionally substituted; and n is 1, 2, 3, 4, 5, 6, 7, 8, 9, or 10.

In certain embodiments, each R is independently H, methyl, ethyl, propyl, i-propyl, butyl, s-butyl, t-butyl, pentyl, hexyl, heptyl, phenyl, benzyl, ethyl phenyl, propyl phenyl, or naphthyl, each of which is optionally substituted.

In other embodiments, each R is independently H, methyl, ethyl, propyl, phenyl, benzyl, 3,3-diphenylpropyl, 2,2-diphenylethyl, or diphenylmethyl.

In various embodiments, each R$_1$, R$_2$, R$_3$, R$_4$, R$_5$, and R$_6$ are H.

In another embodiment, each R$_7$, R$_8$, and R$_9$ are H.

In another embodiment, each n is independently 1, 2, 3, 4, 5, or 6.

In another aspect, the invention provides a pharmaceutical composition comprising a therapeutically effective amount of a compound of formula I or formula II, or a pharmaceutically acceptable salt, solvate or hydrate thereof, in combination with a pharmaceutically acceptable carrier or excipient.

Representative compounds include, but are not limited to, the following compounds of Table 1:

TABLE 1

Structures of compounds 3-33, and inhibition of LSD1 in vitro following treatment with each analogue at 10 μM.

| Compound | Compound | % LSD1 activity remaining |
|---|---|---|
| (structure) | 3 | 74.8 |
| (structure) | 4 | 49.5 |
| (structure) | 5 | 49.2 |
| (structure) | 6 | 40 |
| (structure) | 7 | 100 |
| (structure) | 8 | 79 |

TABLE 1-continued

Structures of compounds 3-33, and inhibition of LSD1 in vitro following treatment with each analogue at 10 μM.

| Compound | Compound | % LSD1 activity remaining |
|---|---|---|
| [structure] 2 HCl | 9 | 89.6 |
| [structure] 2 HCl | 10 | 35.9 |
| [structure] 2 HCl | 11 | 95.9 |
| [structure] 2 HCl | 12 | 91.5 |
| [structure] 2 HCl | 13 | 52.1 |
| [structure] 2 HCl | 14 | 65.5 |
| [structure] 2 HCl | 15 | 60.5 |
| [structure] 2 HCl | 16 | 51.3 |
| [structure] 2 HCl | 17 | 100 |

TABLE 1-continued
Structures of compounds 3-33, and inhibition of LSD1 in vitro following treatment with each analogue at 10 μM.
| Compound | Compound | % LSD1 activity remaining |
|---|---|---|
| 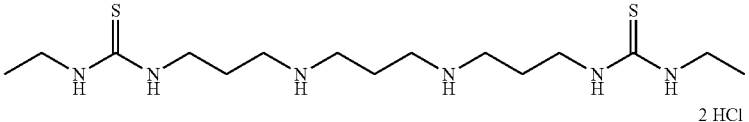 [SMILES: CCNC(=S)NCCCNCCCNCCCNC(=S)NCC ; "2 HCl"] 2 HCl | 18 | 36.2 |
| 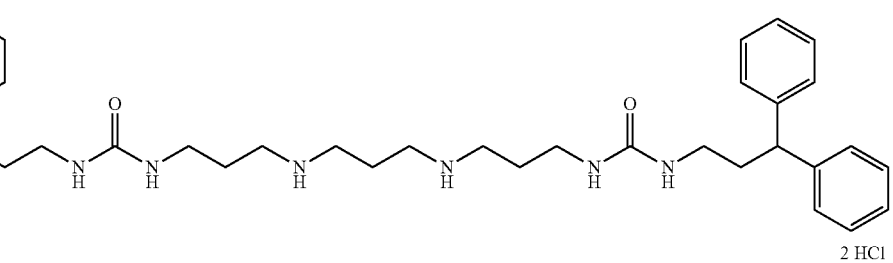 2 HCl | 19 | 92.9 |
| 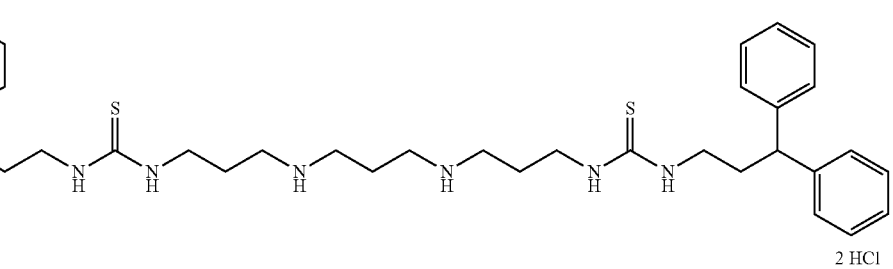 2 HCl | 20 | 92.2 |
| 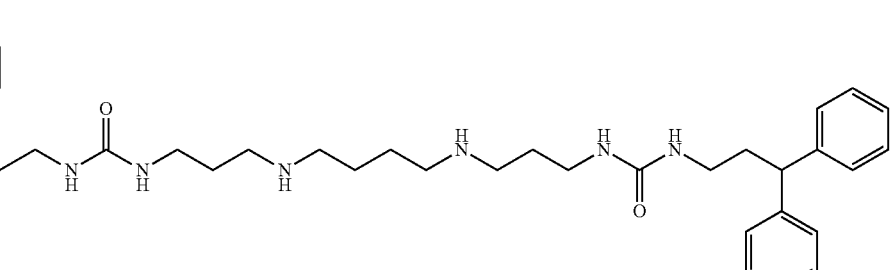 2 HCl | 21 | 74.6 |
| 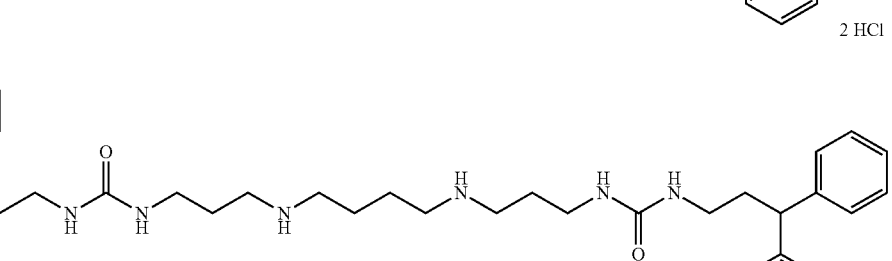 2 HCl | 22 | 88.6 |
| 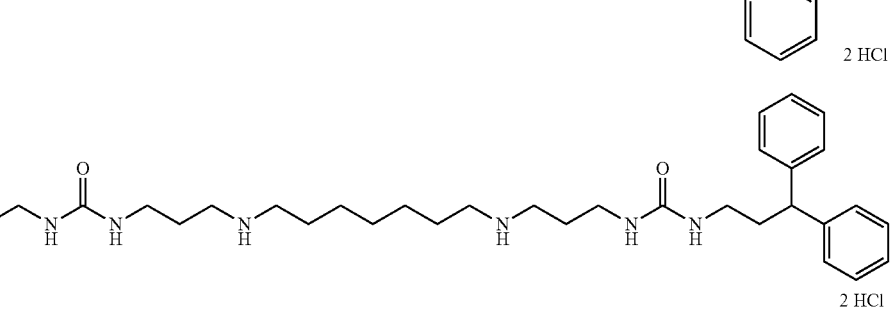 2 HCl | 23 | 51.5 |

TABLE 1-continued

Structures of compounds 3-33, and inhibition of LSD1 in vitro following treatment with each analogue at 10 μM.

| Compound | Compound # | % LSD1 activity remaining |
|---|---|---|
| (structure) 2 HCl | 24 | 77.3 |
| (structure) 2 HCl | 25 | 19.5 |
| (structure) 2 HCl | 26 | 17.1 |
| (structure) 2 HCl | 27 | 24.8 |
| (structure) 2 HCl | 28 | 51.1 |

TABLE 1-continued

Structures of compounds 3-33, and inhibition of LSD1 in vitro following treatment with each analogue at 10 μM.

| Compound | Compound | % LSD1 activity remaining |
|---|---|---|
| (structure) · 2 HCl | 29 | 34.4 |
| (structure) · 2 HCl | 30 | 28.9 |
| (structure) · 2 HCl | 31 | 26.1 |
| (structure) · 2 HCl | 32 | 70 |
| (structure) · 2 HCl | 33 | 91.5 |

In another aspect, the invention provides a pharmaceutical composition comprising a therapeutically effective amount of a compound of the invention, or an embodiment or example described herein, or a pharmaceutically acceptable salt, solvate, hydrate, ester, or prodrug thereof, in combination with a pharmaceutically acceptable carrier or excipient.

Yet another aspect of the present invention is a process of making any of the compounds delineated herein employing any of the synthetic means delineated herein.

Biological Data

Figure 2:
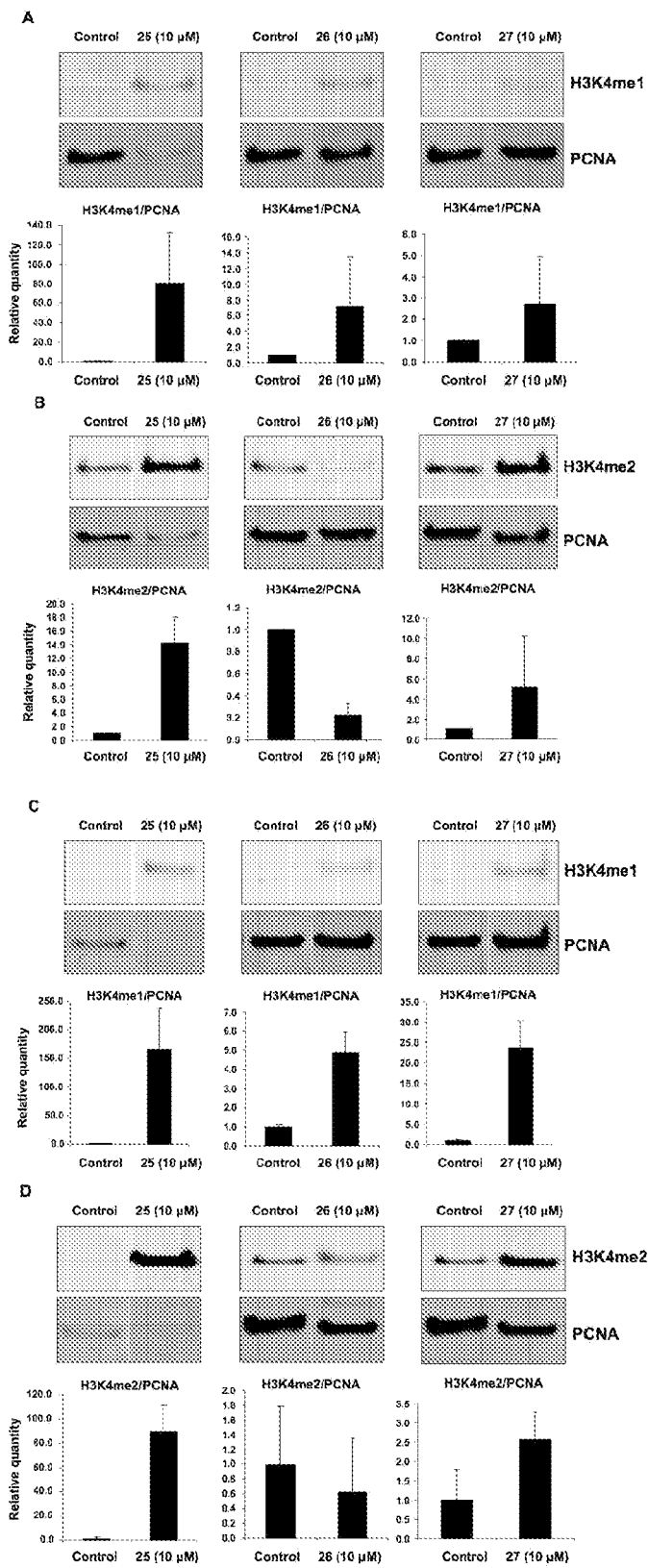
FIG. 2. Effect of compounds 25-27 on the expression of global H3K4me1 and H3K4me2. Calu-6 human anaplastic non-small cell lung carcinoma cells were treated with a 10 μM concentration of 25, 26 or 27 for 24 h (panel A and B) or 48 h (panel C and D) as described below. Panel A and C shows global H3K4me1 expression and panel B and D shows global H3K4me2 expression. Proliferating cell nuclear antigen (PCNA) was used as a loading control. Shown are Western blot images from a single representative experiment performed in triplicate. Relative protein expression levels were determined by quantitative Western analysis using the Odyssey infrared detection system shown as bar graphs. The results represent the mean of three treatments ±SD. The protein expression level for control samples was set to a value of 1.

The ability of the target (bis)ureas and (bis)thioureas to inhibit LSD1 was determined in an assay procedure utilizing the recombinant human enzyme. Expression and purification of LSD1 were conducted as previously reported. Enzymatic activity of LSD1 in the presence of target compounds was determined using luminol-dependent chemiluminescence to measure the production of $H_2O_2$, as previously described. The results of these experiments are summarized in Table 1, and graphically in FIG. 1. As previously observed, compound 2d at 10 mM reduced LSD1 activity by 82.9%. 11 analogues (ureas 4 and 5, thioureas 6, 10, 18, 25, 26, 27, 29 and 30 and the disubstituted carbamoylurea 31) reduced LSD1 activity by 50% or greater at 10 mM concentration (FIG. 1). The three most effective LSD1 inhibitors, compounds 25-27, were chosen for additional studies as outlined below. Subsequent experiments were conducted in the Calu-6 human anaplastic non-small cell lung carcinoma line because it has a highly reproducible response to epigenetic modulation, and because it is known that various tumor suppressor genes are silenced in this line. In order for synthetic analogues to be effective at the cellular level, any observed decreases in cellular LSD1 activity should be accompanied by an increase in global H3K4me1 and H3K4me2 content. Thus, the ability of compounds 25, 26 and 27 to produce increases in global H3K4me1 and H3K4me2 levels was measured as previously described. The results of these studies are shown in FIG. 2. At 24 hours, analogues 25 and 27 produced significant increases in both H3K4me1 (FIG. 2, Panel A) and H3K4me2 (FIG. 2, Panel B), while analogue 26 induced a significant increase in H3K4me1, but decreased the relative amount of H3K4me2. A similar pattern was observed at 48 hours (FIG. 2, Panels C and D). Compound 25 produced the most dramatic increases in H3K4me1 and H3K4me2 at both 24 and 48 hours. The reduction in H3K4me2 and corresponding increase in H3K4me1 by 26 at both 24 and 48 hours cannot be readily explained, and is the subject of continuing investigation. However, this anomolous finding seem to correlate with the observed cytotoxicity of 26 (see below). These data strongly suggest that intracellular inhibition of LSD1 by 25-27 leads to significant increases in methylation at the H3K4 chromatin mark. It is noteworthy that in HCT116 human colon tumor cells, compounds 25-27 all produced at least a 2-fold increase in global H3K4me2 (data not shown), with the most effective analogue being compound 25 (17.4-fold increase).

Figure 3:
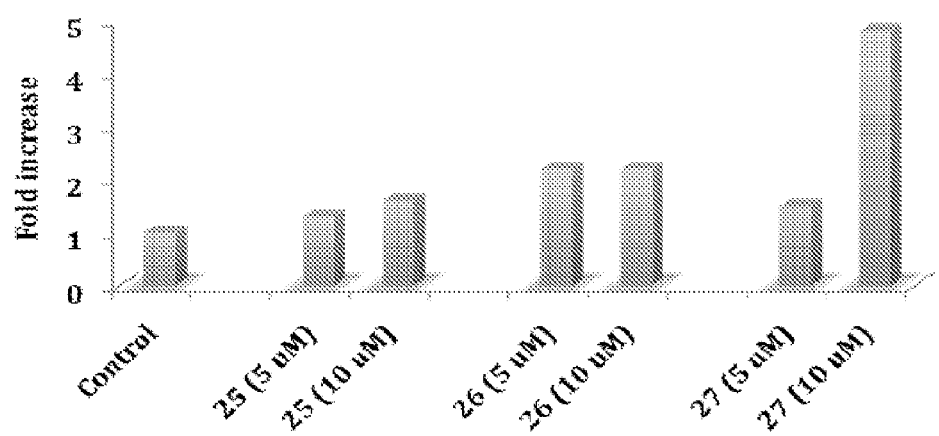
FIG. 3. Effect of compounds 25-27 on the re-expression of secreted frizzle-related protein 2 (SFRP2, Panel A) and the transcription factor GATA4 (Panel B) mRNA. Calu-6 human anaplastic non-small cell lung carcinoma cells were treated with either a 5 or 10 mM concentration of 25, 26 or 27 for 24 hours as described in the methods section. cDNA was then synthesized from mRNA, amplified and measured by qPCR. Each data point is the average of 3 determinations that differed in all cases by 5% or less.
Figure 3:
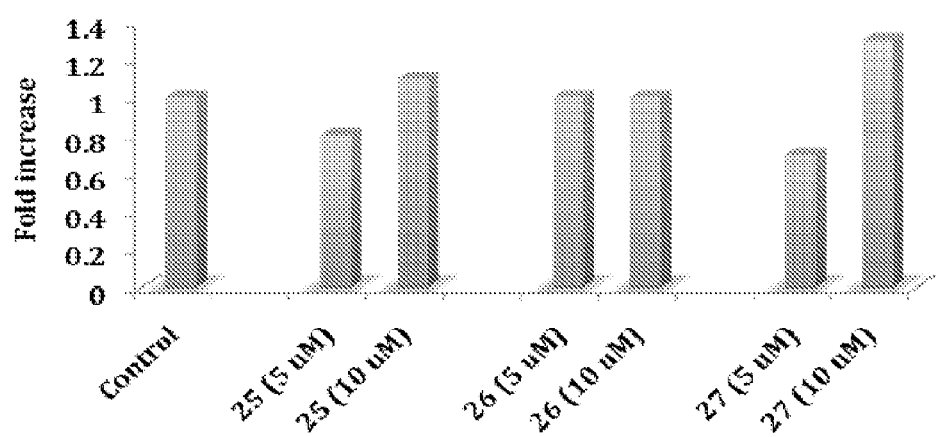

The ability of compounds 25-27 to induce the re-expression of aberrantly silenced tumor suppressor genes in vitro was next measured using the Calu-6 human lung carcinoma cell line. The tumor suppressor genes SFRP2 and GATA4 were chosen because they are known to be under expressed in human lung cancer, and because they are thought to play a role in tumorigenesis when silenced. Thus, the genes coding for these proteins are well-documented LSD1 targets. Cells were treated for 24 hours with either a 5 or 10 mM concentration of 25, 26 or 27, after which the levels of secreted frizzle-related protein (SFRP) 2, a soluble modulator of Wnt signaling, and the zinc-finger transcription factor GATA4, were determined by quantitative PCR (qPCR). The results of these studies are shown in FIG. 3. All three compounds produced increases in SFRP2 expression that appeared to be dose dependent for 25 and 27 (FIG. 3A). Compound 27 produced the largest increase in SFRP2 expression at 10 mM (4.8-fold increase). Compounds 25 and 26 did not produce significant increases in GATA4 levels at 5 and 10 µM (FIG. 3B), and compound 27 induced a 1.3-fold increase in GATA4 mRNA at 10 µM, and had no significant effect at 5 µM (FIG. 2B). The increase in GATA4 mRNA caused by 10 mM 27 is reproducible, but is not statistically significant (P>0.05).

Figure 4:
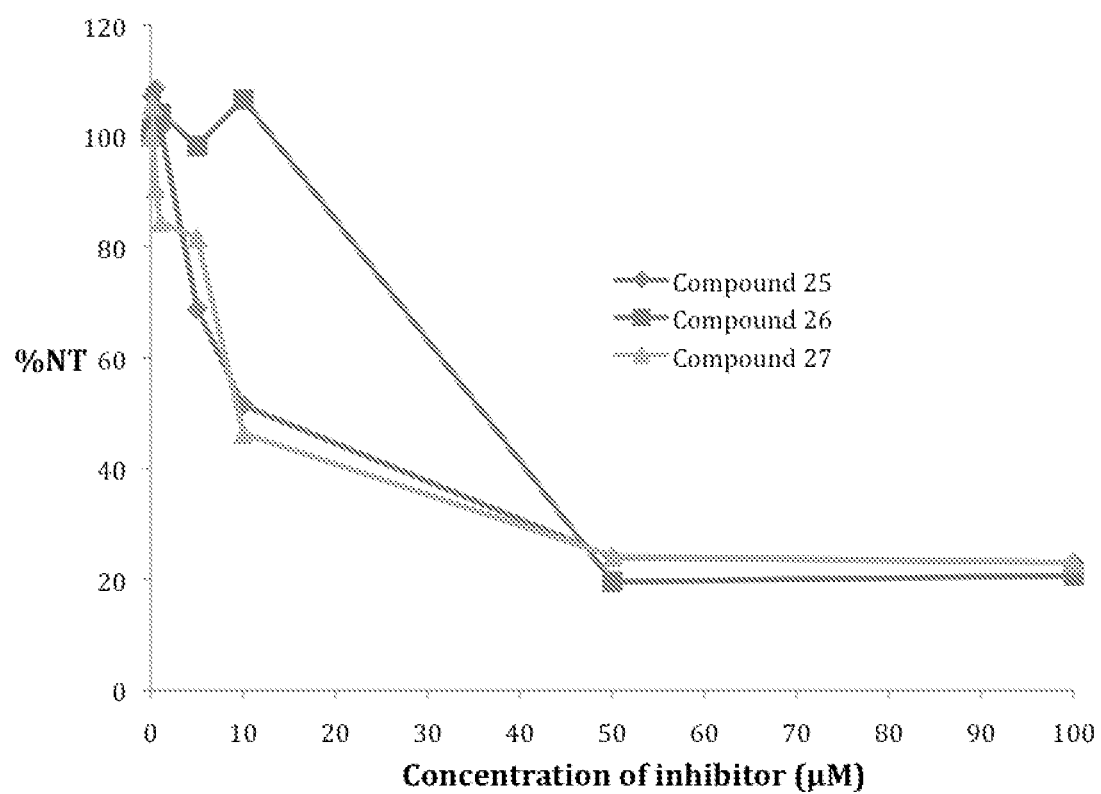
FIG. 4. Effect of compounds 25-27 on Calu-6 human anaplastic non-small cell lung carcinoma cell viability as measured by standard MTS assay. Cells were treated with increasing concentrations of each test compound for 96 hours prior to measurement of cell viability. % NT refers to the percent of viable cells remaining at time T (96 hours) as compared to the number of cells seeded, $N_0$. Each data point is the average of 3 determinations that differed in all cases by 5% or less.

The (3-(4,5-dimethylthiazol-2-yl)-5-(3-carboxymethoxyphenyl)-2-(4-sulfophenyl)-2H-tetrazolium) (MTS) reduction assay was used to determine the effects of compounds 25-27 on cell viability in the Calu-6 cell line. Cells were treated with increasing concentrations of each test compound for 96 hours prior to measurement of cell viability, and growth inhibition ($GI_{50}$) values were then determined from the resulting dose-response curve. As seen in FIG. 4, compounds 25, 26 and 27 produced moderate reduction in cell viability, with $GI_{50}$ values of 10.3, 38.3 and 9.4 mM, respectively.

The potential LSD1 inhibitors 3-33 were synthesized using pathways that are facile and relatively inexpensive, and that can be used to introduce chemical diversity into the resulting urea and thiourea analogues, thus making them suitable for generation of a library of related ureas and thioureas. Our initial series of guanidine and biguanide derivatives represented the first novel small molecule inhibitors of LSD1 with potential for development as therapeutic agents. The current studies suggest that replacement of the imine NH functionality of the terminal guanidine in 1c with oxygen or sulfur is an allowable isosteric change, and active analogues in both the urea and thiourea series were identified (FIG. 1). However, the sulfur isosteric replacement is likely more acceptable, since the 6 best LSD1 inhibitors (6, 10, 18, and 25-27) were all thioureas. A more bulky aromatic substituent on the terminal nitrogen, as in 25-27, appears to impart greater activity than the smaller alkyl or benzyl substituents found in 6, 10 and 18. There did not appear to be predictable differences in activity between analogues with 3, 4 or 7 carbon central chains, suggesting that this parameter may not have a great influence on inhibition of the enzyme. This is especially apparent among 25-27 (terminal N-substituent=2,2-diphenylethyl), which have 7, 4 and 3 carbon central regions, respectively, but vary in activity by less than 5%. However, by contrast, among compounds 28-30 (terminal N-substituent=1,1-diphenylmethyl), inhibitory potency did appear to be proportional to the length of the internal carbon chain. In addition to the urea and thiourea derivatives, the carbamoylurea 31, designed as an analogue of 2d, also produces potent inhibition of LSD1 (73.9% at 10 mM). Additional analogues will need to be synthesized and evaluated to generate a more accurate set of structure/activity relationships for this series of compounds.

The inhibitory effects of 25-27 on LSD1 (FIG. 1), combined with the observed methylation levels at the H3K4 chromatin mark (FIG. 2A-D) strongly suggest that LSD1 is inhibited in the Calu-6 tumor cell line, resulting in increases in the substrates H3K4me1 and H3K4me2. The anomolous reduction in H3K4me2 at 24 and 48 hours caused by 26 are unexpected.

Compounds 25-27 were next evaluated for the ability to induce the re-expression of SFRP2 and GATA4 mRNA, as determined by qPCR from treated Calu-6 human lung carcinoma cells. In the case of SFRP2, all three analogues induced increases of the protein between 1.3- and 4.8-fold (FIG. 3A). These increases appeared to be dose-dependent, except in the case of 26, which induced same level of SFRP2 expression at both 5 and 10 µM. The order of potency in this regard was 27>26>25. Compound 27 produced 1.3-fold increase in GATA4 expression at 10 mM that was not statistically significant, and 25-27 at all other concentrations produced no effect on GATA4 mRNA. The observed increases in SFRP2 re-expression following treatment with 25-27, and the increase in GATA4 re-expression induced by 10 mM 27, are consistent with the previously reported effects of the parent compounds 1c and 2d. The disparity in the ability of 25-27 to induce SFRP2 expression, but not GATA4 expression, suggests that LSD1 inhibition may have variable effects at different gene promoters.

As discussed above, compounds 25-27 proved to be only moderately cytotoxic in the Calu-6 non-small cell lung carcinoma line in vitro. Compounds 25 and 27 produced the most prominent reduction in cell viability, exhibiting $GI_{50}$ values of 10.3 and 9.4 mM, respectively. In addition, these $GI_{50}$ values are in the range of the histone deacetylase (HDAC) inhibitor MS-275, as measured in three colon tumor cell lines. Compound 26 was significantly less cytotoxic, exhibiting a $GI_{50}$ value of 38.3 mM. Our data suggests that decreases in H3K4me2 at 24 and 48 hours and/or minimal effects on the re-expression of SFRP2 and GATA4 by 26 could account for this reduced cytotoxicity. It is important to note that epigenetic modulators such as those mentioned above are generally used in combination with traditional cytotoxic agents, and serve to restore the ability of transformed cells to undergo apoptosis. As such, cytotoxicity is less of an issue, as long as the compound produces epigenetic effects in tumor cells that can be exploited by traditional cytotoxic agents.

Methods of Treatment

In certain aspects, the invention provides a method of treating a disease or disorder associated with lysine-specific demethylase 1 (LSD1) in a subject, the method comprising the step of administering to the subject an effective amount of a compound of formula I or formula II, or a pharmaceutically acceptable salt, ester or hydrate thereof.

In another aspect, the invention provides a method of treating a disease or disorder associated with lysine-specific demethylase 1 (LSD1) in a subject, wherein the subject is identified as being in need of a LSD1 inhibitor, the method comprising the step of administering to the subject an effective amount of a compound of formula I or formula II, or a pharmaceutically acceptable salt, ester or hydrate thereof.

In certain embodiments, the disease or disorder is selected from: tumor, cancer, neoplasia, skin disorders, neovascularization, inflammatory and arthritic diseases, retinoblastoma, cystoid macular edema (CME), exudative age-related macular degeneration (AMD), diabetic retinopathy, diabetic macular edema, or ocular inflammatory disorders.

In a further embodiment, the disease or disorder is cancer.

In a further embodiment, the disease or disorder is ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain/cns cancer, throat cancer, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

In another aspect, the invention provides a method of inhibiting or reducing lysine-specific demethylase 1 (LSD1) in a subject, the method comprising the step of administering to the subject an effective amount of a compound of formula I or formula II; wherein said compound is identified in a screening assay.

In certain embodiments, the screening assay is a demethylase assay.

In other embodiments, the LSD1 inhibitor has a $IC_{50}$ for inhibiting LSD1 less than about 5 micromolar.

In another aspect, the invention provides a method of treating tumor, cancer, or neoplasia in a subject, the method comprising the step of administering to the subject an effective amount of a compound of formula I or formula II, or a pharmaceutically acceptable salt, solvate or hydrate thereof.

In certain embodiments, the compound inhibits LSD1 to thereby treat the tumor, cancer, or neoplasia.

In various embodiments, the invention provides a method as described herein, further comprising an additional therapeutic agent.

In certain embodiments, the additional therapeutic agent is a LSD1 inhibiting compound.

In a further embodiment, the additional therapeutic agent is an anticancer compound.

In other embodiments, the invention provides a method as described herein, wherein the step of administering the compound comprises administering the compound orally, topically, parentally, intravenously or intramuscularly.

In a further embodiment, the step of administering the compound comprises administering the compound in a dosage of between about 0.1 and 120 mg/kg/day.

In a further embodiment, the step of administering the compound comprises administering the compound in a dosage of less than about 500 mg/day.

In other embodiments, the invention provides any method as described herein, wherein the subject is a human.

In another aspect, the invention provides a kit comprising an effective amount of a compound of formula I or formula II in unit dosage form, together with instructions for administering the compound to a subject suffering from or susceptible to a LSD1-related disease.

In certain embodiments, the invention provides a compound, composition, kit, or method of treatment as described herein, wherein the compound of the invention is selected from any of the formulae as described here, e.g., formula I, formula II, formula I-a, I-b, I-c, I-d, formula II-a, II-b, II-c, II-d, or is selected from a compound in Table 1.

In certain embodiments, the invention provides a method wherein the disease or disorder associated with LSD1 is a skin disorder.

In a further embodiment, the disease or disorder is psoriasis, acne, rosacea, warts, eczema, hemangiomas, lymphangiogenesis, Sturge-Weber syndrome, venous ulcers of the skin, neurofibromatosis, and tuberous sclerosis.

In another embodiment, the invention provides a method wherein the disease or disorder associated with LSD1 is neovascularization.

In a further embodiment, the disease or disorder is malaria, diabetic retinopathy, retinopathy of prematurity, corneal graft rejection, neovascular glaucoma, retrolental fibroplasias, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, *Mycobacteria* infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, corneal graft rejection, macular edema, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme disease, systemic lupus erythematosus, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications, and diseases associated with rubeosis (neovascularization of the ankle).

In other embodiments, the invention provides a method wherein the disease or disorder associated with LSD1 is inflammatory and arthritic disease.

In a further embodiment, the disease or disorder is: rheumatoid arthritis, osteoarthritis, lupus, scleroderma, Crohn's disease, ulcerative colitis, psoriasis, sarcoidosis, Sarcoidosis, skin lesions, hemangiomas, Osler-Weber-Rendu disease, hereditary hemorrhagic telangiectasia, and osteoarthritis.

In another embodiment, the invention provides a method wherein the disease or disorder affects the dermis, epidermis, endometrium, retina, surgical wound, gastrointestinal tract, umbilical cord, liver, kidney, reproductive system, lymphoid system, central nervous system, breast tissue, urinary tract, circulatory system, bone, muscle, or respiratory tract.

An inhibitory amount or dose of the compounds of the present invention may range from about 0.1 mg/Kg to about 500 mg/Kg, alternatively from about 1 to about 50 mg/Kg. Inhibitory amounts or doses will also vary depending on route of administration, as well as the possibility of co-usage with other agents.

The term "inhibitory amount" of a compound of the present invention means a sufficient amount to decrease the cancer in a biological sample or a subject. It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin, which may be intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present invention comprise administration to a patient in need of such treatment from about 10 mg to about 1000 mg of the compound(s) of this invention per day in single or multiple doses. In another embodiment, the treatment regimen comprises administration to a patient in need of such treatment from about 25 mg to about 6000 mg of a compound(s) of this invention per day in single or multiple doses. For instance a compound of the present invention can be administered to a patient twice a day with a total daily dose of 4000, 4200, 4400, 4600, 4800 or 5000 mg.

Definitions

Listed below are definitions of various terms used to describe this invention. These definitions apply to the terms as they are used throughout this specification and claims, unless otherwise limited in specific instances, either individually or as part of a larger group. The number of carbon atoms in a hydrocarbyl substituent can be indicated by the prefix "$C_x$—$C_y$," where x is the minimum and y is the maximum number of carbon atoms in the substituent. Likewise, a $C_x$ chain means a hydrocarbyl chain containing x carbon atoms.

The prefix "halo" indicates that the substituent to which the prefix is attached is substituted with one or more independently selected halogen radicals. For example, "$C_1$-$C_6$haloalkyl" means a $C_1$-$C_6$alkyl substituent wherein at least one hydrogen radical is replaced with a halogen radical.

If a linking element in a depicted structure is "absent", then the left element in the depicted structure is directly linked to the right element in the depicted structure. For example, if a chemical structure is depicted as X-(L)$_n$-Y wherein L is absent or n is 0, then the chemical structure is X-Y.

The term "alkyl" as used herein, refers to a saturated, straight- or branched-chain hydrocarbon radical. For example, "$C_1$-$C_8$ alkyl" contains from one to eight carbon atoms. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds. For example, "$C_2$-$C_8$ alkynyl" contains from from two to eight carbon atoms. Representative alkynyl groups include, but are not limited to, for example, ethynyl, 1-propynyl, 1-butynyl, heptynyl, octynyl and the like.

The term "cycloalkyl" denotes a monovalent group derived from a monocyclic or polycyclic saturated carbocyclic ring compound. Examples of cycloalkyl include, but not limited to, cyclopropyl, cyclobutyl, cyclopentyl, cyclohexyl, bicyclo[2.2.1]heptyl, and bicyclo[2.2.2]octyl and the like. The terms "carbocycle" or "carbocyclic" or "carbocyclyl" refer to a saturated (e.g., "cycloalkyl"), partially saturated (e.g., "cycloalkenyl" or "cycloalkynyl") or completely unsaturated (e.g., "aryl") ring system containing zero heteroatom ring atom. A carbocyclyl may be, without limitation, a single ring, or two or more fused rings, or bridged or spiro rings. A carbocyclyl may contain, for example, from 3 to 10 ring members (i.e., $C_3$-$C_{10}$carbocyclyl, such as $C_3$-$C_{10}$cycloalkyl). A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, fluorenyl, indanyl, 1,2,3,4-tetrahydro-naphthyl, indenyl, isoindenyl, bicyclodecanyl, anthracenyl, phenanthrene, benzonaphthenyl (also known as "phenalenyl"), decalinyl, and norpinanyl and the like. A carbocyclyl group can be attached to the parent molecular moiety through any substitutable carbon atom of the group.

The term "aryl" refers to an aromatic carbocyclyl containing from 6 to 14 carbon ring atoms. Non-limiting examples of aryls include phenyl, naphthalenyl, anthracenyl, and indenyl and the like. An aryl group can be connected to the parent molecular moiety through any substitutable carbon atom of the group.

The term "heteroaryl" means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The term "heterocycloalkyl" refers to a non-aromatic 3-, 4-, 5-, 6- or 7-membered ring or a bi- or tri-cyclic group fused system, where at least one of the ring atoms is a heteroatom, and where (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl and the like.

The terms "heterocyclic" or "heterocycle" or "heterocyclyl" refer to a saturated (e.g., "heterocycloalkyl"), partially unsaturated (e.g., "heterocycloalkenyl" or "heterocycloalkynyl") or completely unsaturated (e.g., "heteroaryl") ring system, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results. A heterocyclyl may be, without limitation, a single ring. Non-limiting examples of single-ring heterocyclyls include furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, or diazepinyl. A heterocyclyl may also include, without limitation, two or more rings fused together, such as, for example, naphthyridinyl, thiazolpyrimidinyl, thienopyrimidinyl, pyrimidopyrimidinyl, or pyridopyrimidinyl. A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

The terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I,

—OH, protected hydroxy, alkoxy, oxo, thiooxo,

—$NO_2$, —CN, $CF_3$, $N_3$,

—$NH_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O— alkyl, —O— alkenyl, —O— alkynyl, —O— cycloalkyl, —O-aryl, —O-heteroaryl, —O— heterocyclic, —C(O)— alkyl, —C(O)— alkenyl, —C(O)— alkynyl, —C(O)— cycloalkyl, —C(O)-aryl, —C(O)— heteroaryl, —C(O)-heterocycloalkyl, —$CONH_2$, —CONH— alkyl, —CONH— alkenyl, —CONH— alkynyl, —CONH— cycloalkyl, —CONH-aryl, —CONH-heteroaryl, —CONH-heterocycloalkyl, —$OCO_2$— alkyl, —$OCO_2$— alkenyl, —$OCO_2$— alkynyl, —$OCO_2$— cycloalkyl, —$OCO_2$-aryl, —$OCO_2$-heteroaryl, —$OCO_2$-heterocycloalkyl, —$OCONH_2$, —OCONH— alkyl, —OCONH— alkenyl, —OCONH— alkynyl, —OCONH— cycloalkyl, —OCONH— aryl, —OCONH— heteroaryl, —OCONH— heterocycloalkyl, —NHC(O)— alkyl, —NHC(O)— alkenyl, —NHC(O)— alkynyl, —NHC(O)— cycloalkyl, —NHC(O)-aryl, —NHC(O)-heteroaryl, —NHC(O)-heterocycloalkyl, —$NHCO_2$— alkyl, —$NHCO_2$— alkenyl, —$NHCO_2$— alkynyl, —$NHCO_2$-cycloalkyl, —$NHCO_2$— aryl, —$NHCO_2$— heteroaryl, —$NHCO_2$— heterocycloalkyl, —$NHC(O)NH_2$, —NHC(O)NH— alkyl, —NHC(O)NH— alkenyl, —NHC(O)NH— alkynyl, —NHC(O)NH— cycloalkyl, —NHC(O)NH-aryl, —NHC(O)NH-heteroaryl, —NHC(O)NH-heterocycloalkyl, $NHC(S)NH_2$, —NHC(S)NH— alkyl, —NHC(S)NH— alkenyl, —NHC(S)NH— alkynyl, —NHC(S)NH— cycloalkyl, —NHC(S)NH-aryl, —NHC(S)NH-heteroaryl, —NHC(S)NH-heterocycloalkyl, —NHC(NH)NH$_2$, —NHC(NH)NH— alkyl, —NHC(NH)NH— -alkenyl, —NHC(NH)NH— alkenyl, —NHC(NH)NH— cycloalkyl, —NHC(NH)NH-aryl, —NHC(NH)NH-heteroaryl, —NHC(NH)NH-heterocycloalkyl, —NHC(NH)— alkyl, —NHC(NH)— alkenyl, —NHC(NH)— alkenyl, —NHC(NH)— cycloalkyl, —NHC(NH)-aryl, —NHC(NH)— heteroaryl, —NHC(NH)-heterocycloalkyl, —C(NH)NH— alkyl, —C(NH)NH— alkenyl, —C(NH)NH— alkynyl, —C(NH)NH— cycloalkyl, —C(NH)NH-aryl, —C(NH)NH-heteroaryl, —C(NH)NH-heterocycloalkyl, —S(O)— alkyl, —S(O)— alkenyl, —S(O)— alkynyl, —S(O)— cycloalkyl, —S(O)-aryl, —S(O)— heteroaryl, —S(O)-heterocycloalkyl —SO$_2$NH$_2$, —SO$_2$NH— alkyl, —SO$_2$NH— alkenyl, —SO$_2$NH— alkynyl, —SO$_2$NH— cycloalkyl, —SO$_2$NH— aryl, —SO$_2$NH— heteroaryl, —SO$_2$NH— heterocycloalkyl, —NHSO$_2$— alkyl, —NHSO$_2$— alkenyl, —NHSO$_2$— alkynyl, —NHSO$_2$— cycloalkyl, —NHSO$_2$— aryl, —NHSO$_2$-heteroaryl, —NHSO$_2$-heterocycloalkyl, —CH$_2$NH$_2$, —CH$_2$SO$_2$CH$_3$, -alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— cycloalkyl, —S-aryl, —S-heteroaryl, —S-heterocycloalkyl, or methylthiomethyl.

It is understood that the aryls, heteroaryls, carbocycles, heterocycles, alkyls, and the like can be further substituted.

The terms "halo" and "halogen," as used herein, refer to an atom selected from fluorine, chlorine, bromine and iodine.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

The term "leaving group," or "LG", as used herein, refers to any group that leaves in the course of a chemical reaction involving the group and includes but is not limited to halogen, brosylate, mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, Protective Groups in Organic Synthesis, 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, Protective Groups in Organic Synthesis, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "alkylamino" refers to a group having the structure —N(R$_a$R$_b$), where R$_a$ and R$_b$ are independent H or alkyl.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

As used herein, "solvate" refers to the physical association of a compound of the invention with one or more solvent molecule, whether organic or inorganic. This physical association often includes hydrogen bonding. In certain instances, the solvate is capable of isolation, for example, when one or more solvate molecules are incorporated in the crystal lattice of the crystalline solid.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups, and elixirs. In addition to the active compounds, the liquid dosage forms may contain inert diluents commonly used in the art such as, for example, water, alcohol or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, polysorbate, dimethylformamide, oils (in particular, cottonseed, groundnut, corn, germ, olive, castor, and sesame oils), mono- or diglycerides, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, antioxidants, sweetening, flavoring, and perfuming agents. The liquid dosage form can also be encapsulated in a gelatin capsule, wherein a compound of the present invention can be dissolved in a pharmaceutically acceptable carrier containing, for example, one or more solubilizing agents (e.g., polysorbate 80 and mono and diglycerides), and other suitable excipients (e.g., an antioxidants such as ascorbyl palmitate, or a sweetening or flavoring agent).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Immediate release forms are also contemplated by the present invention.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above.

The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Preferably, a compound of the invention is formulated in a solid dispersion, where the compound can be molecularly dispersed in a matrix which comprises a pharmaceutically acceptable, hydrophilic polymer. The matrix may also contain a pharmaceutically acceptable surfactant. Suitable solid dispersion technology for formulating a compound of the invention includes, but is not limited to, melt extrusion, spray drying, or solvent evaporation.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, cancer is treated in a subject, such as a human or another animal, by administering to the subject a therapeutically effective amount of a compound of the invention (or a pharmaceutically acceptable salt, ester or prodrug thereof), in such amounts and for such time as is necessary to achieve the desired result. The term "therapeutically effective amount" of a compound of the invention, as used herein, means a sufficient amount of the compound so as to decrease the subject's symptoms. As is well understood in the medical arts a therapeutically effective amount of a compound of this invention will be at a reasonable benefit/risk ratio applicable to any medical treatment.

Synthetic Methods

The compounds and processes of the present invention will be better understood in connection with the following synthetic schemes that illustrate the methods by which the compounds of the invention may be prepared.

Definitions of variables in the structures in the schemes herein are commensurate with those of corresponding positions in the formulae delineated herein.

Preparation of compounds 3-33 depended on the availability of the appropriate isocyanates and isothiocyanates. All of these intermediates were commercially available, with the exception of isocyanate 35c and isothiocyanates 37a-c, which were synthesized as shown in Scheme 1. Isocyanate 35c could be made in a single step by reacting the requisite diphenylalkylamine 34c (m=2) with trichloroacetic anhydride (toluene, $N_2$, reflux) for 5 hours. To produce the corresponding isothiocyanates 37a-c (m=0, 1 or 2, respectively), amines 34a-c were allowed to react with carbon disulfide in the presence of triethylamine in THF at 5° C. The reaction was allowed to warm to room temperature, and after 3 hours the intermediate dithiocarbamates 36a-c could be isolated. Reaction of the intermediate dithiocarbamates 36a-c with tosyl chloride in THF then afforded the desired isothiocyanates 37a-c.

Scheme 1

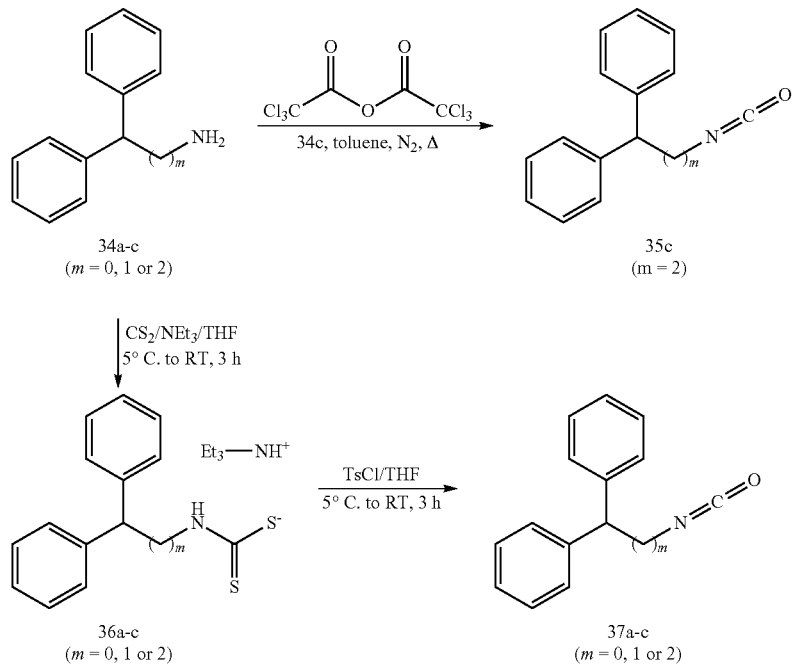

To access a library of isosteric urea and thiourea analogues related to 1c and 2d, we employed our previously published synthesis of precursor molecules 41a-c, as shown in Scheme 2. The appropriate diamine 38a, 38b or 38c was (bis)cyanoethylated (acrylonitrile, EtOH, reflux) to afford the corresponding (bis)cyano intermediates 39a-c. The central nitrogens in 39a-c were then N-Boc protected ((Boc)$_2$O, CH$_2$Cl$_2$/Aq. NaHCO$_3$) to form 40a-c, and the cyano groups were reduced (Raney Ni) to yield the desired diamines 41a-c. Compounds 41a-c were then reacted with the appropriate isocyanates or isothiocyanates 42d-z, 42aa-ee, 35c and 37a-c to produce the corresponding protected (bis)ureas or (bis)thioureas 43d-z and 43aa-ee, followed by acid removal of the N-Boc protection groups (HCl in EtOAc) to afford the desired urea or thiourea products 3-30.

In order to access isosteric derivatives of the (bis)biguanide lead compound 2d, the synthetic route outlined in Scheme 3 was devised. Initially, primary amines of general structure 44 were reacted with N-chlorocarbonyl isocyanate 45, with the intention of forming the alkyl N-chlorocarbonylurea 46. However, this reaction could not be controlled, even at low temperature, to produce the monoalkylated derivative 46, but immediately formed the bis-alkylated (bis)biguanide 47. In order to form the desired monoalkylated product, it was necessary to use a less reactive secondary amine in the initial step. Thus diphenylamine 48 was added to N-chlorocarbonyl isocyanate 45, and the mixture was stirred for 20 minutes to form a mixture of 49 and the bis-alkylated product 50. Addition of compounds 41a, b or c to this reaction mixture in the presence of triethylamine produced the bis-N-Boc-protected precursors 51-53, which were separated from 50 by silica gel chromatography. Acid-catalyzed removal of the N-Boc protecting groups in 51-53 then afforded the desired target compounds 31-33. Importantly, the syntheses described in Schemes 1-3 can be adapted to produce a wide variety of analogues with chemical diversity in the length of the alkyl chains, and in the terminal alkyl- or aralkyl substituents.

Scheme 2

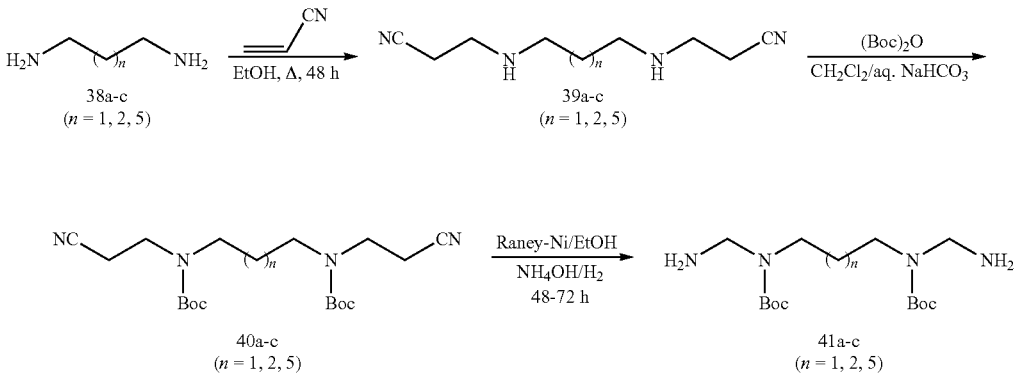

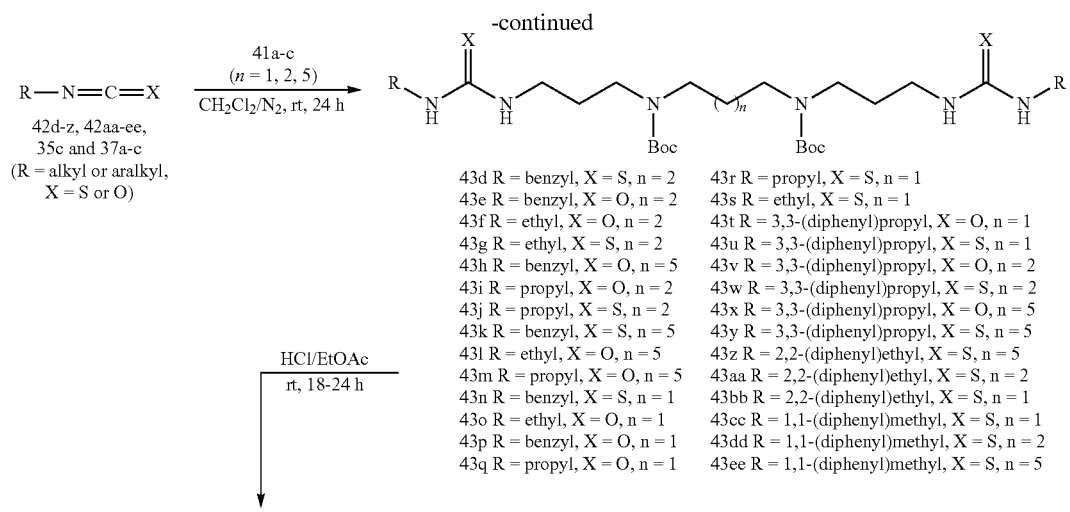

43d R = benzyl, X = S, n = 2
43e R = benzyl, X = O, n = 2
43f R = ethyl, X = O, n = 2
43g R = ethyl, X = S, n = 2
43h R = benzyl, X = O, n = 5
43i R = propyl, X = O, n = 2
43j R = propyl, X = S, n = 2
43k R = benzyl, X = S, n = 5
43l R = ethyl, X = O, n = 5
43m R = propyl, X = O, n = 5
43n R = benzyl, X = S, n = 1
43o R = ethyl, X = O, n = 1
43p R = benzyl, X = O, n = 1
43q R = propyl, X = O, n = 1
43r R = propyl, X = S, n = 1
43s R = ethyl, X = S, n = 1
43t R = 3,3-(diphenyl)propyl, X = O, n = 1
43u R = 3,3-(diphenyl)propyl, X = S, n = 1
43v R = 3,3-(diphenyl)propyl, X = O, n = 2
43w R = 3,3-(diphenyl)propyl, X = S, n = 2
43x R = 3,3-(diphenyl)propyl, X = O, n = 5
43y R = 3,3-(diphenyl)propyl, X = S, n = 5
43z R = 2,2-(diphenyl)ethyl, X = S, n = 5
43aa R = 2,2-(diphenyl)ethyl, X = S, n = 2
43bb R = 2,2-(diphenyl)ethyl, X = S, n = 1
43cc R = 1,1-(diphenyl)methyl, X = S, n = 1
43dd R = 1,1-(diphenyl)methyl, X = S, n = 2
43ee R = 1,1-(diphenyl)methyl, X = S, n = 5

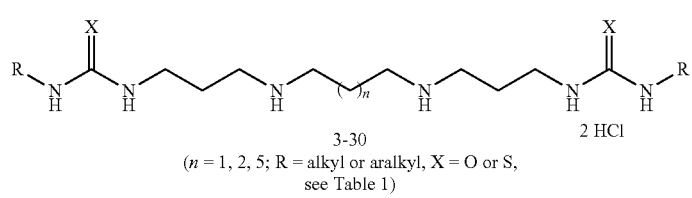

3-30
($n$ = 1, 2, 5; R = alkyl or aralkyl, X = O or S, see Table 1)

Scheme 3

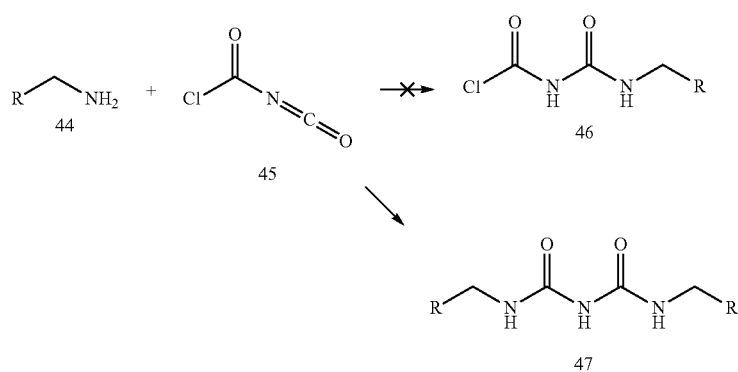

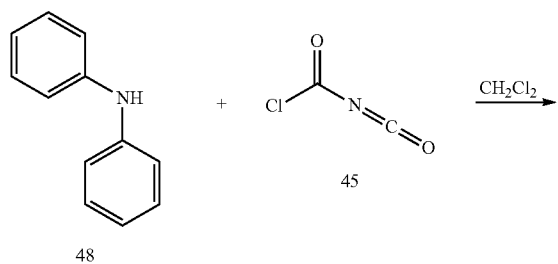

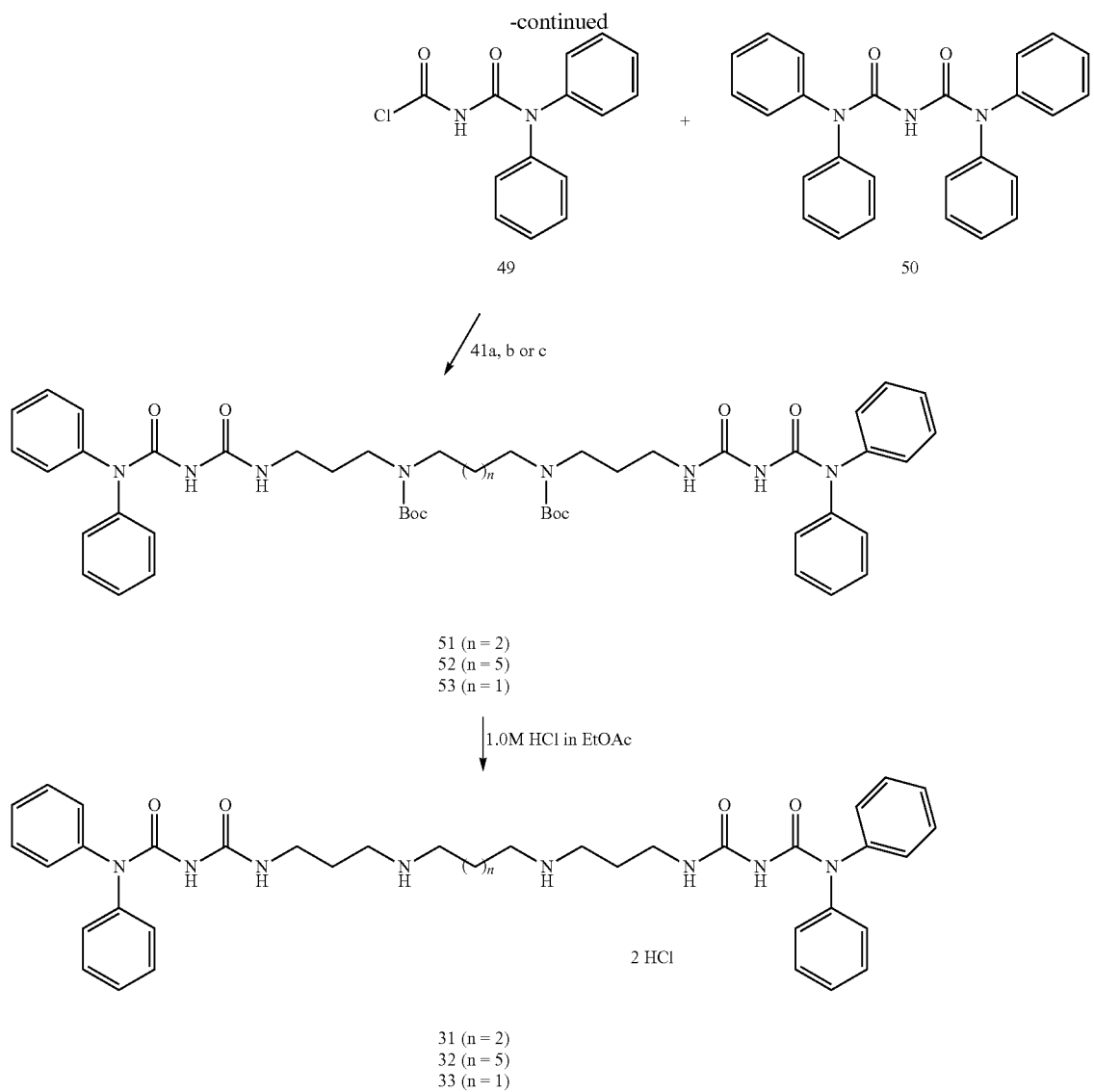

51 (n = 2)
52 (n = 5)
53 (n = 1)

31 (n = 2)
32 (n = 5)
33 (n = 1)

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transfor-* mations, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

The compounds and processes of the present invention will be better understood in connection with the following examples, which are intended as an illustration only and not to limit the scope of the invention. The following examples can be prepared according to the schemes as described above, or according to the synthetic steps as described below. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The chemical structures herein contain certain —NH—, —NH$_2$ (amino) and —OH (hydroxyl) groups where the corresponding hydrogen atom(s) may not explicitly appear; however they are to be read as —NH—, —NH$_2$ or —OH as the case may be.

All reagents and dry solvents were purchased from Aldrich Chemical Co. (Milwaukee, Wis.), Sigma Chemical Co. (St. Louis, Mo.) or Acros Chemical (Chicago, Ill.) and were used without further purification except as noted below. Pyridine was dried by passing it through an aluminum oxide column and then stored over KOH. Triethylamine was distilled from potassium hydroxide and stored in a nitrogen atmosphere. Methanol was distilled from magnesium and iodine under a nitrogen atmosphere and stored over molecular sieves. Methylene chloride was distilled from phosphorus pentoxide and chloroform was distilled from calcium sulfate. Tetrahydrofuran was purified by distillation from sodium and benzophenone. Dimethyl formamide was dried by distillation from anhydrous calcium sulfate and was stored under nitrogen. Preparative scale chromatographic procedures were carried out using E. Merck silica gel 60, 230-440 mesh. Thin layer chromatography was conducted on Merck precoated silica gel 60 F-254. Ion exchange chromatography was conducted on Dowex 1X8-200 anion exchange resin. Compounds 41a-c were synthesized as previously described.

All $^1$H— and $^{13}$C-NMR spectra were recorded on a Varian Mercury 400 mHz spectrometer, and all chemical shifts are reported as δ values referenced to TMS or DSS. Infrared spectra were recorded on a Jasco FT-IR spectrophotometer and are referenced to polystyrene. In all cases, $^1$H-NMR, $^{13}$C-NMR and IR spectra were consistent with assigned structures. Mass spectra were recorded on a Kratos MS 80 RFA (EI and CI) or Kratos MS 50 TC (FAB) mass spectrometer. Prior to biological testing, target molecules 3-33 were determined to be 95% pure or greater by HPLC chromatography using an Agilent Series 1100 high-performance liquid chromatograph fitted with a C18 reversed-phase column.

Synthetic H3K4me2 peptides were purchased from Millipore (Billerica, Mass.). Calu-6 cells were maintained in RPMI medium, both supplemented with 10% fetal bovine serum (Gemini Bio-Products, Woodland, Calif.) and grown at 37° C. in 5% CO$_2$ atmosphere.

Example 1

Isocyanate Intermediates 3,3-Diphenylpropylisocyanate (35c)

A 4.24 g (0.020 mol) portion of 3,3-diphenylpropylamine was dissolved in 90 mL of dry toluene in a 250 mL round-bottomed flask under a nitrogen atmosphere, and triphosgene (2.98 g, 0.010 mol) was added to the reaction mixture. The reaction mixture was heated under reflux for 5 h and then cooled to room temperature, at which time an additional 0.5 g of triphosgene was added. The reaction was then stirred for an additional 18 h at room temperature. During this time, the formation of product was monitored by TLC using hexane:ethyl acetate (3:1). When the reaction was complete, activated charcoal (0.50 g) was carefully added into reaction mixture to decolorize the solution, which was stirred for 30 min and filtered. The filtrate was concentrated under reduced pressure to give a light pale yellow semi-solid. A 100 mL portion of n-hexane/ethyl ether (1:1 ratio) was then added, and the mixture was stirred for 15 minutes. The solution was filtered and concentrated to afford 4.23 g of viscous material. The crude product was purified by flash chromatography on silica gel eluted with dichloromethane to furnish 3,3-diphenylpropylisocyanate 35c as a white solid (1.31 g, 28% yield). $^1$H NMR (CDCl$_3$): δ 7.38-7.10 (m, 10H, Ar—H), 4.09 (t, 1H, J=7.2 Hz, CHPh$_2$), 3.27 (t, 2H, J=6.4 Hz, CH$_2$NCS), 2.36 (m, 2H, CH$_2$CH$_2$); $^{13}$C NMR (CDCl$_3$): δ 143.69, 128.94, 128.01, 126.85 (Ar—C), 48.14, 41.51, 36.87 (CH and CH$_2$).

Example 2

General Procedure for Preparation of Isothiocyanates 37a-c 3,3-Diphenylpropylisothiocyanate (37c)

In a 250 mL round-bottomed flask under a nitrogen atmosphere, 3,3-diphenylpropylamine 34c (2.10 g, 0.010 mol) was dissolved in 40 mL of freshly distilled THF, 3.64 g (5.0 mL, 0.036 mol) of triethylamine was added, and the mixture was cooled to 5° C. in an ice bath. Carbon disulfide (0.76 g, 0.96 mL, 0.10 mol) was then added to the reaction mixture via syringe over 20 min. Following addition of carbon disulfide, the mixture was stirred an additional 30 min, warmed to room temperature and allowed to stir a further 2 h. A $^1$H NMR of an aliquot (after removing the solvent in vacuo) indicated that conversion to the dithiocarbamate salt 36c was complete. $^1$H NMR (DMSO-d$_6$): δ 8.46 (t, 1H, NH), 7.34-7.12 (m, 8H, Ar—H), 7.06 (t, 2H, Ar—H), 3.94 (t, 1H, CHPh$_2$), 3.34 (m, 2H, CH$_2$NCS), 3.04 (q, 6H, NCH$_2$CH$_3$), 2.24 (m, 2H, CH$_2$CH$_2$), 1.20 (t, 6H, NCH$_2$CH$_3$).

The reaction mixture from above was re-cooled in an ice bath, 2.38 g of tosyl chloride (0.012 mol) was added, and the reaction mixture was allowed to stir for 30 min at 5° C. It was then warmed to room temperature and stirred for an additional 3 h. The solvent was removed in vacuo, the reaction was partitioned between 40 mL of 1.0 N HCl and 150 mL of Et$_2$O, and the two-phased mixture was stirred for 10 min. The organic layer was separated and the aqueous layer was extracted with a 100 mL portion of Et$_2$O. The combined organic layers was dried over Na$_2$SO$_4$, and concentrated to produce a viscous oil that solidified during vacuum drying. The product was purified by flash chromatography on silica gel (eluted with CH$_2$Cl$_2$) to give 37c as a white solid (1.48 g, 53% based on 34c, TLC Rf: 0.45 (n-hexane/EtOAc, 9:1). $^1$H NMR (CDCl$_3$): δ 7.32-7.19 (m, 10H, Ar—H), 4.08 (t, 1H, J=8.0 Hz, CHPh$_2$), 3.44 (t, 2H, J=6.8 Hz, CH$_2$NCS), 2.41 (m, 2H, CH$_2$CH$_2$); $^{13}$C NMR (CDCl$_3$): δ 143.17, 129.08, 127.97, 126.99 (Ar—C), 48.12, 43.66, 35.69 (CH and CH$_2$).

1,1-Diphenylmethylisothiocyanate (37a)

Isothiocyanate 37a was prepared from 1,1-diphenylethylamine 34a and carbon disulfide using the procedure described above for the synthesis of 37c. The product was isolated as a white solid in 70% yield. TLC Rf: 0.90 (n-hexane/MeCO$_2$Et, 4:1). $^1$H NMR (CDCl$_3$): δ 7.40-7.31 (m, 10H, Ar—H), 5.99 (s, 1H, CHPh$_2$); $^{13}$C NMR (CDCl$_3$): δ 139.43, 129.18, 128.57, 126.85 (Ar—C), 64.82 (CH).

2,2-Diphenylethylisothiocyanate (37b)

Isothiocyanate 37b was prepared from 1,1-diphenylethylamine 34a and carbon disulfide using the procedure described above for the synthesis of 37c. The product was isolated as a white solid in 87% yield. $^1$H NMR (DMSO-d$_6$): δ 7.36-7.29 (m, 8H, Ar—H), 7.24-7.20 (t, 2H, J=7.2 Hz, Ar—H), 4.45 (t, 1H, J=8.0 Hz, CHPh$_2$), 4.34 (d, 2H, J=7.6 Hz, CH$_2$NCS); $^{13}$C NMR (DMSO-d$_6$): δ 1 41.64, 129.31, 128.53, 127.67 (Ar—C), 51.18, 48.95 (CH and CH$_2$).

Example 3

General Procedure for Preparation of N-Boc Protected (bis)thioureas 1,12-bis-{3-[1-(benzyl)thioureado]}-4,9-[N-(tertbutyl)oxycarbonyl)]-4,9-diazadodecane (43d)

In a 100 mL round-bottom flask, a 0.3 g portion of 4,9-[N-(tertbutyl)oxycarbonyl)]-4,9-diaza-1,12-diaminododecane 41b (0.0008 mol) was dissolved in 20 mL of HPLC grade CH$_2$Cl$_2$ under a nitrogen atmosphere and the mixture was cooled to 0° C. A solution of benzylisothiocyanate (240 mg, 0.0016 mol) in 5 mL of CH$_2$Cl$_2$ was then added dropwise with stirring, and the reaction mixture was allowed to stir at room temperature for 5 h. During this time, the formation of product was monitored by TLC (CH$_2$Cl$_2$/MeOH/NH$_4$OH 89:10:1). After completion of the reaction, the CH$_2$Cl$_2$ was removed under reduced pressure to produce a viscous colorless oil. The crude product was purified by flash chromatography on silica gel eluted with CH$_2$Cl$_2$/MeOH/NH$_4$OH (94.5:5:0.5 followed by 89:10:1) to furnish pure 43d (0.46 g, 88% yield) as viscous oil. Rf: 0.46 (CH$_2$Cl$_2$/MeOH/NH$_4$OH, 89:10:1). $^1$H NMR (CDCl$_3$): δ 7.31 (m, 10H, Ar—H), 6.31 (b, 2H, NH), 4.55 (bs, 4H, NCH$_2$), 3.54 (bs, 4H, NCH$_2$), 3.20 (bs, 4H, NCH$_2$), 3.10 (bs, 4H, NCH$_2$), 1.65 (bs, 4H, CH$_2$CH$_2$), 1.46 (bs, 4H, CH$_2$CH$_2$), 1.38 (s, 18H, C[CH$_3$]$_3$).

1,12-bis-{3-[1-(ethyl)thioureado]}-4,9-[N-(tertbutyl) oxycarbonyl)]-4,9-diazadodecane (43g)

Compound 43g was prepared from 375 mg of 41b (375 mg, 0.0009 mol) and ethylisothiocyanate, according to procedure described above for the synthesis of 43d to afford 43g (512 mg, 95%) as viscous oil. Rf: 0.52 (CH$_2$Cl$_2$/MeOH/NH$_4$OH, 89:10:1); $^1$H NMR (CDCl$_3$): δ 7.40 (b, 2H, NH), 6.00 (b, 2H, NH), 3.56 (m, 4H, NCH$_2$), 3.34 (b, 4H, NCH$_2$), 3.26 (b, 4H, NCH$_2$), 3.12 (b, 4H, NCH$_2$), 1.71 (b, 4H, CH$_2$CH$_2$), 1.50 (bs, 4H, CH$_2$CH$_2$), 1.40 (s, 18H, C(CH$_3$)$_3$), 1.20 (t, 6H, J=7.2 Hz, CH$_3$). $^{13}$C NMR (CDCl$_3$): δ 80.36 ([CH$_3$]$_3$C), 46.95, 43.34, 41.19, 38.12, 28.63, 27.31, 26.16 (CH$_2$), 14.28 (CH$_3$).

1,12-bis-{3-[1-(propyl)thioureado]}-4,9-[N-(tertbutyl)oxycarbonyl)]-4,9-diazadodecane (43j)

Compound 43j was prepared from 260 mg of 41b (0.0007 mol) and n-propylisothiocyanate according to procedure described above for the synthesis of 43d to afford 43j (380 mg, 96%) as viscous oil. Rf: 0.51 (CH$_2$Cl$_2$/MeOH/NH$_4$OH, 89:10:1). $^1$H NMR (CDCl$_3$): δ3.50-3.36 (b, 8H, NCH$_2$), 3.28-3.20 (m, 8H, NCH$_2$), 3.26 (b, 4H, NCH$_2$) 1.78 (b, 4H, CH$_2$CH$_2$), 1.52 (bs, 4H, CH$_2$CH$_2$), 1.46 (s, 18H, C[CH$_3$]$_3$), 0.73 (t, 6H, J=7.2 Hz, CH$_3$). $^{13}$C NMR (CDCl$_3$): δ80.36 ([CH$_3$]$_3$C), 46.95, 43.34, 41.19, 38.12, 28.63, 27.31, 26.16 (CH$_2$), 14.28 (CH$_3$).

1,15-bis-{3-[1-(benzyl)thioureado]}-4,12-[N-(tertbutyl)oxycarbonyl)]-4,12-diazapentadecane (43k)

Compound 43k was prepared from 220 mg of 41c (0.0005 mol) and benzylisothiocyanate according to procedure described above for the synthesis of 43d to afford 43k (360 mg, 96%) as viscous oil; $^1$H NMR (CDCl$_3$): δ 7.39-7.30 (m, 10H, Ar—H), 4.76 (b, 4H, CH$_2$Ph), 3.46 (b, 4H, NCH$_2$), 3.18 (m, 8H, NCH$_2$), 1.52 (b, 4H, CH$_2$CH$_2$), 1.54 (b, 4H, CH$_2$CH$_2$), 1.44 (s, 18H, C(CH$_3$)$_3$), 1.28 (b, 6H, CH$_2$CH$_2$).

1,11-bis-{3-[1-(benzyl)thioureado]}-4,8-[N-(tertbutyl)oxycarbonyl)]-4,8-diazaundecane (43n)

Compound 43n was prepared from 291 mg of 41a (0.0008 mol) and benzylisothiocyanate according to the procedure described above for 43d to afford 43n (373 mg, 73%) as viscous oil. Rf: 0.87 (CH$_2$Cl$_2$/MeOH/NH$_4$OH, 89:10:1). $^1$H NMR (CDCl$_3$): δ 7.35 (m, 10H, Ar—H), 4.58 (bs, 4H, N—CH$_2$), 3.58 (bs, 4H, N—CH$_2$), 3.21 (b, 4H, N—CH$_2$), 3.10 (b, 4H, N—CH$_2$), 1.72 (b, 6H, CH$_2$CH$_2$), 1.40 (s, 18H, C[CH$_3$]$_3$).

1,11-bis-{3-[1-(propyl)thioureado]}-4,8-[N-(tertbutyl)oxycarbonyl)]-4,8-diazaundecane (43r)

Compound 43r was prepared from 291 mg of 41a (0.0008 mol) and n-propylisothiocyanate according to the procedure described above for 43d to afford 43r (379 mg, 86%) as viscous oil. Rf: 0.57 (CH$_2$Cl$_2$/MeOH/NH$_4$OH, 89:10:1). $^1$H NMR (CDCl$_3$): δ 7.29 (bs, 1H, NH), 6.44 (s, 2H, NH), 3.43 (bs, 4H, N—CH$_2$), 3.01-3.15 (b, 12H, N—CH$_2$), 1.61 (bs, 6H, CH$_2$CH$_2$), 1.47 (m, J=7.2 Hz, 4H, CH$_2$CH$_3$), 1.31 (s, 18H, C[CH$_3$]$_3$), 0.81 (t, J=7.2 Hz, 6H, CH$_2$CH$_3$).

1,11-bis-{3-[1-(n-ethyl)thioureado]}-4,8[N-(tertbutyl)oxycarbonyl)]-4,8-diazaundecane (43s)

Compound 43s was prepared from 291 mg of 41a (0.0008 mol) and ethylisothiocyanate according to the procedure described above for 43d to afford 43s (347 mg, 83%) as viscous oil. Rf: 0.72 (CH$_2$Cl$_2$/MeOH/NH$_4$OH, 89:10:1). $^1$H NMR (CDCl$_3$): δ 7.24 (bs, 2H, NH), 6.22 (bs, 2H, NH), 3.49 (bs, 4H, CH$_2$N), 3.29 (bs, 4H, N—CH$_2$), 3.20 (b, 4H, N—CH$_2$), 3.07 (b, 4H, N—CH$_2$), 1.62-1.74 (b, 6H, CH$_2$CH$_2$), 1.37 (s, 18H, C[CH$_3$]$_3$), 1.14 (t, 6H, CH$_2$CH$_3$).

1,11-bis-{3-[1-(3,3-diphenylpropyl)thioureado]}-4,8-[N-(tertbutyl)oxycarbonyl)]-4,8-diazaundecane (43u)

Compound 43u was prepared from 155 mg of 41a (0.0004 mol) and 37c according to procedure described above for the synthesis of 43d to afford 43u (290 mg, 81%) as a white solid. Rf: 0.44 (CH$_2$Cl$_2$/MeOH/NH$_4$OH, 89:10:1); $^1$H NMR (CDCl$_3$): δ 7.29-7.15 (m, 22H, Ar—H, and NH), 5.88 (b, 2H, NH), 4.04 (t, 2H, J=7.6 Hz, CHPh$_2$), 3.53 (b, 4H, NCH$_2$), 3.28 (b, 4H, NCH$_2$), 3.23 (b, 4H, NCH$_2$), 3.12 (b, 8H, NCH$_2$), 2.36 (q, 4H, J=8.0 Hz, NCH$_2$), 1.70 (m, 2H, CH$_2$CH$_2$), 1.47 (b, 4H, CH$_2$CH$_2$), 1.40 (s, 20H, C[CH$_3$]$_3$).

1,12-bis-{3-[1-(3,3-diphenylpropyl)thioureado]}-4,9-[N-(tertbutyl)oxycarbonyl)]-4,9-diazadodecane (43w)

Compound 43w was prepared from 161 mg of 41b (0.0004 mol) and 37c according to procedure described above for the synthesis of 43d to afford 43w (322 mg, 89%) as a white solid. Rf: 0.52 (CH$_2$Cl$_2$/MeOH/NH$_4$OH, 89:10:1); $^1$H NMR (CDCl$_3$): δ 7.25-7.16 (m, 22H, Ar—H, and NH), 5.88 (b, 2H, NH), 4.02 (t, 2H, J=8.0 Hz, CHPh$_2$), 3.17 (b, 8H, NCH$_2$), 3.09 (b, 4H, NCH$_2$), 2.37 (q, 4H, J=7.6 Hz, CH$_2$CH), 1.76-1.65 (m, 8H, CH$_2$CH$_2$), 1.41 (s, 18H, C[CH$_3$]$_3$).

1,15-bis-{3-[1-(3,3-diphenylpropyl)thioureado]}-4,12-[N-(tertbutyl)oxycarbonyl)]-4,12-diazapentadecane (43y)

Compound 43y was prepared from 178 mg of 41c (0.0004 mol) and 37c according to procedure described above for the synthesis of 43d to afford 43y (305 mg, 80%) as a white solid. Rf: 0.57 (CH$_2$Cl$_2$/MeOH/NH$_4$OH, 89:10:1). $^1$H NMR (CDCl$_3$): δ 7.28-7.15 (m, 20H, Ar—H), 5.88 (b, 2H, NH), 4.02 (t, 2H, J=8.0 Hz, CHPh$_2$), 3.54 (b, 4H, NCH$_2$), 3.28 (b, 4H, NCH$_2$), 3.23 (b, 4H, NCH$_2$), 3.08 (t, 4H, J=7.2 Hz, NCH$_2$), 2.36 (q, 4H, J=7.6 Hz, CH$_2$CH), 1.69 (bs, 4H, CH$_2$CH$_2$), 1.50 (b, 4H, CH$_2$CH$_2$), 1.40 (s, 18H, C[CH$_3$]$_3$), 1.28 (m, 6H, CH$_2$CH$_2$).

1,15-bis-{3-[1-(2,2-diphenylethyl)thioureado]}-4,12-[N-(tertbutyl)oxycarbonyl)]-4,12-diazapentadecane (43z)

Compound 43z was prepared from 223 mg of 41c (0.0005 mol) and 37b according to procedure described above for the synthesis of 43d to afford 43z (288 mg, 79%) as a white solid. Rf: 0.68 (CH$_2$Cl$_2$/MeOH/NH$_4$OH, 89:10:1). $^1$H NMR (CDCl$_3$): δ 7.31-7.19 (m, 20H, Ar—H), 5.75 (b, 2H, NH), 4.28 (b, 2H, CHPh$_2$), 4.02 (b, 4H, NCH$_2$), 3.54 (b, 4H, NCH$_2$), 3.25 (b, 4H, NCH$_2$), 3.09 (t, 4H, J=7.2 Hz, NCH$_2$), 1.69 (bs, 4H, CH$_2$CH$_2$), 1.49 (b, 4H, CH$_2$CH$_2$), 1.40 (bs, 18H, C[CH$_3$]$_3$), 1.24 (m, 6H, CH$_2$CH$_2$).

1,12-bis-{3-[1-(2,2-diphenylethyl)thioureado]}-4,9-[N-(tertbutyl)oxycarbonyl)]-4,9-diazadodecane (43aa)

Compound 43aa was prepared from 161 mg of 41b (0.0004 mol) and 37b according to procedure described above for the synthesis of 43d to afford 43aa (295 mg, 84%) as a white solid. Rf: 0.60 (CH$_2$Cl$_2$/MeOH/NH$_4$OH, 89:10:1). $^1$H NMR (CDCl$_3$): δ 7.32-7.20 (m, 20H, Ar—H), 5.77 (b, 2H, NH), 4.29 (b, 2H, CHPh$_2$), 4.02 (b, 4H, NCH$_2$), 3.56 (bs, 4H, NCH$_2$), 3.26 (bs, 4H, NCH$_2$), 3.12 (bs, 4H, NCH$_2$), 1.70 (b, 4H, CH$_2$CH$_2$), 1.48 (b, 4H, CH$_2$CH$_2$), 1.41 (s, 18H, C[CH$_3$]$_3$).

1,11-bis-{3-[1-(2,2-diphenylethyl)thioureado]}-4,9-[N-(tertbutyl)oxycarbonyl)]-4,9-diazadodecane (43bb)

Compound 43bb was prepared from 193 mg (0.0005 mol) of 41b and 37b according to procedure described above for the synthesis of 43d to afford 43bb (350 mg, 80%) as a white solid. Rf: 0.63 (CH$_2$Cl$_2$/MeOH/NH$_4$OH, 89:10:1). $^1$H NMR (CDCl$_3$): δ 7.32-7.20 (m, 20H, Ar—H), 5.77 (bs, 2H, NH), 4.29 (bs, 2H, CHPh$_2$), 4.02 (bs, 4H, NCH$_2$), 3.56 (bs, 4H, NCH$_2$), 3.26 (bs, 4H, NCH$_2$), 3.12 (t, 4H, J=7.2 Hz, NCH$_2$), 1.71 (b, 4H, CH$_2$CH$_2$), 1.41 (b, 20H, CH$_2$ and C[CH$_3$]$_3$).

1,11-bis-{3-[1-(1,1-diphenylmethyl)thioureado]}-4,8-[N-(tertbutyl)oxycarbonyl)]-4,8-diazaundecane (43 cc)

Compound 43 cc was prepared from 192 mg of 41a (0.0005 mol) and 37a according to procedure described above for the synthesis of 43d to afford 43 cc as a white solid (350 mg, 83%), Rf: 0.63 (CH$_2$Cl$_2$/MeOH/NH$_4$OH, 89:10:1). $^1$H NMR (CDCl$_3$): δ 7.34-7.27 (m, 20H, Ar—H), 6.43 (d, 2H, J=5.2 Hz, NCH), 6.02 (b, 2H, NH), 3.52 (d, 4H, J=5.2 Hz, NCH$_2$), 3.06 (m, 8H, NCH$_2$), 1.66 (bs, 6H, CH$_2$CH$_2$), 1.36 (bs, 18H, C[CH$_3$]$_3$).

1,12-bis-{3-[1-(1,1-diphenylmethyl)thioureado]}-4,9-[N-(tertbutyl)oxycarbonyl)]-4,9-diazadodecane (43dd)

Compound 43dd was prepared from 201 mg of 41b (0.0005 mol) and 37a according to procedure described above for the synthesis of 43d to afford 43dd (380 mg, 89%) as white solid. Rf: 0.60 (CH$_2$Cl$_2$/MeOH/NH$_4$OH, 89:10:1). $^1$H NMR (CDCl$_3$): δ 7.40 (b, 2H, NH), 7.34-7.27 (m, 20H, Ar—H), 6.43 (d, 2H, J=5.2 Hz, NCH), 6.02 (b, 2H, NH), 3.52 (d, 4H, J=5.2 Hz, NCH$_2$), 3.06 (bs, 8H, NCH$_2$), 1.63 (m, 4H, CH$_2$CH$_2$), 1.42 (bs, 4H, CH$_2$CH$_2$), 1.36 (s, 18H, C[CH$_3$]$_3$).

1,15-bis-{3-[1-(1,1-diphenylmethyl)thioureado]}-4,12-[N-(tertbutyl)oxycarbonyl)]-4,12-diazapentadecane (43ee)

Compound 43ee was prepared from 223 mg of 41c and 37a according to procedure described above for the synthesis of 43d to afford 43ee (408 mg, 91%) as a white solid. Rf: 0.77 (CH$_2$Cl$_2$/MeOH/NH$_4$OH, 89:10:1); $^1$H NMR (CDCl$_3$): δ 7.45 (b, 2H, NH), 7.33-7.26 (m, 20H, Ar—H), 6.41 (d, 2H, J=2.8 Hz, NCH), 6.03 (b, 2H, NH), 3.51 (m, 4H, NCH$_2$), 3.04 (m, 8H, NCH$_2$), 1.54 (bs, 4H, CH$_2$CH$_2$), 1.45 (b, 4H, CH$_2$CH$_2$), 1.35 (bs, 18H, C[CH$_3$]$_3$), 1.23 (m, 6H, CH$_2$CH$_2$).

Example 4

General Procedure for Preparation of N-Boc Protected (Bis)Ureas 1,12-bis-{3-[1-(benzyl)ureado]}-4,9-[N-(tertbutyl) oxycarbonyl)]-4,9-diazadodecane (43e)

In a 100 mL round-bottom flask, a 0.35 g portion of 4,9-[N-(tertbutyl)oxycarbonyl)]-4,9-1,12-diamino-diazadodecane 41b (0.0009 mol) was dissolved in 20 mL of HPLC grade CH$_2$Cl$_2$ under a nitrogen atmosphere and the mixture was cooled to 0° C. A solution of benzylisocyanate (0.235 g, 0.0018 mol) in 5 mL of CH$_2$Cl$_2$ was then added dropwise with stirring, and the reaction mixture was allowed to stir at room temperature for 24 h. During this time, the formation of product was monitored by TLC (CH$_2$Cl$_2$:MeOH:NH$_4$OH 89:10:1). When the starting material had been consumed, the CH$_2$Cl$_2$ was removed under reduced pressure to afford a viscous colorless material. The crude product was purified by flash chromatography on silica gel eluted with CH$_2$Cl$_2$:MeOH:NH$_4$OH (97:2.5:0.5 followed by 94.5:5.0:0.5) to furnish pure 43e (0.50 g, 86% yield) as viscous oil. Rf: 0.54 (CH$_2$Cl$_2$/MeOH/NH$_4$OH, 89:10:1); $^1$H NMR (CDCl$_3$): δ 3.20-3.02 (m, 16H, NCH$_2$), 1.64 (b, 4H, CH$_2$CH$_2$), 1.48 (b, 4H, CH$_2$CH$_2$), 1.43 (s, 18H, C[CH$_3$]$_3$), 1.11 (t, 6H, J=6.4 Hz, CH$_3$).

1,12-bis-{3-[1-(ethyl)ureado]}-4,9-[N-(tertbutyl) oxycarbonyl)]-4,9-diazadodecane (43f)

Compound 43f was prepared from 368 mg of 41b (0.0009 mol) and ethylisocyanate according to the procedure described above for 43e to afford 43f (480 mg, 96%) as viscous oil. Rf: 0.54 (CH$_2$Cl$_2$/MeOH/NH$_4$OH, 89:10:1). $^1$H NMR (CDCl$_3$): δ 3.20-3.02 (m, 16H, NCH$_2$), 1.64 (b, 4H, CH$_2$CH$_2$), 1.48 (b, 4H, CH$_2$CH$_2$), 1.43 (s, 18H, C[CH$_3$]$_3$), 1.11 (t, 6H, J=6.4 Hz, CH$_3$).

1,15-bis-{3-[1-(benzyl)ureado]}-4,12-[N-(tertbutyl) oxycarbonyl)]-4,12-diazapentadecane (43h)

Compound 43h was prepared from 230 mg of 41b (0.0005 mol) and benzylisocyanate according to the procedure described above for 43e to afford 43h (350 mg, 96%) as viscous oil. Rf: 0.50 (CH$_2$Cl$_2$/MeOH/NH$_4$OH, 89:10:1). $^1$H NMR (CD$_3$OD): δ 7.30 (m, 10H, Ar—H), 4.29 (s, 4H, CH$_2$Ph), 3.21-3.15 (m, 8H, NCH$_2$), 3.12 (t, 4H, J=7.2 Hz, NCH$_2$), 1.70 (bs, 4H, CH$_2$CH$_2$), 1.50 (bs, 4H, CH$_2$CH$_2$), 1.44 (s, 18H, C[CH$_3$]$_3$), 1.32 (bs, 6H, CH$_2$CH$_2$).

1,12-bis-{3-[1-(propyl)ureado]}-4,9-[N-(tertbutyl) oxycarbonyl)]-4,9-diazadodecane (43i)

Compound 43i was prepared from 260 mg of 41c (0.0005 mol) and n-propylisocyanate according to the procedure described above for 43e to afford 43i (356 mg, 94%) as viscous oil. Rf: 0.54 (CH$_2$Cl$_2$/MeOH/NH$_4$OH, 89:10:1). $^1$H NMR (CD$_3$OD): δ 3.22 (m, 8H, NCH$_2$), 3.09 (t, 4H, J=6.4 Hz, NCH$_2$), 3.05 (t, 4H, J=7.6 Hz, NCH$_2$), 1.70 (b, 4H, CH$_2$CH$_2$), 1.50 (m, 8H, CH$_2$CH$_2$), 1.45 (s, 18H, C[CH$_3$]$_3$), 0.90 (t, 6H, J=7.6 Hz, CH$_3$).

1,15-bis-{3-[1-(benzyl)ureado]}-4,12-[N-(tertbutyl) oxycarbonyl)]-4,12-diazapentadecane (43l)

Compound 43l was prepared from 225 mg of 41c (0.0005 mol) and ethylisocyanate according to the procedure described above for 43e to afford 43l (280 mg, 94%) as viscous oil. Rf: 0.37 (CH$_2$Cl$_2$/MeOH/NH$_4$OH, 89:10:1). $^1$H NMR (CD$_3$OD): δ 3.28-3.12 (m, 8H, NCH$_2$), 3.10-3.06 (m, 8H, NCH$_2$), 1.68 (b, 4H, CH$_2$CH$_2$), 1.54 (b, 4H, CH$_2$CH$_2$), 1.44 (s, 18H, C[CH$_3$]$_3$), 1.30 (b, 6H, CH$_2$CH$_2$), 1.08 (t, 6H, J=7.2 Hz, CH$_2$CH$_2$).

1,15-bis-{3-[1-(propyl)ureado]}-4,12-[N-(tertbutyl) oxycarbonyl)]-4,12-diazapentadecane (43m)

Compound 43m was prepared from 225 mg of 41c (0.0005 mol) and propylisocyanate according to the procedure described above for 43e to afford 43m (280 mg, 92%) as viscous oil. Rf: 0.35 (CH$_2$Cl$_2$/MeOH/NH$_4$OH, 89:10:1). $^1$H NMR (CD$_3$OD): δ 3.25-3.16 (m, 8H, NCH$_2$), 3.09-3.02 (m, 8H, NCH$_2$), 1.68 (b, 4H, CH$_2$CH$_2$), 1.52 (b, 8H, CH$_2$CH$_2$), 1.44 (s, 18H, C[CH$_3$]$_3$), 1.30 (b, 6H, CH$_2$CH$_2$), 0.90 (t, 6H, J=7.2 Hz, CH$_2$CH$_2$).

1,11-bis-{3-[1-(ethyl)ureado]}-4,8-[N-(tertbutyl) oxycarbonyl)]-4,8-diazaundecane (43o)

Compound 43o was prepared from 287 mg of 41a (0.0007 mol) and ethylisothiocyanate according to the procedure described above for 43e to afford 43o (245 mg, 62%) as viscous oil, Rf: 0.63 (CH$_2$Cl$_2$/MeOH/NH$_4$OH, 89:10:1); $^1$H NMR (CDCl$_3$): δ 5.59 (bs, 1H, NH), 4.60 (bs, 1H, NH), 3.08-3.31 (m, 16H, N—CH$_2$), 1.58-1.78 (m, 6H, CH$_2$CH$_2$), 1.43 (s, 18H, C[CH$_3$]$_3$), 1.10 (t, J=7.2 Hz, 6H, CH$_2$CH$_3$).

1,11-bis-{3-[1-(benzyl)ureado]}-4,8-[N-(tertbutyl) oxycarbonyl)]-4,8-diazaundecane (43p)

Compound 43p was prepared from 302 mg of 41a (0.0008 mol) and benzylisothiocyanate according to the procedure described above for 43e to afford 43p (485 mg, 95%) as viscous oil, Rf: 0.63 (CH$_2$Cl$_2$/MeOH/NH$_4$OH, 89:10:1); $^1$H NMR (CDCl$_3$): δ 7.10-7.30 (m, 10H, Ar—H), 4.20 (bs, 4H, PhCH$_2$), 2.98-3.20 (m, 12H, N—CH$_2$), 1.65 (p, 2H, CH$_2$CH$_2$), 1.55 (p, J=6.4 Hz, 4H, CH$_2$CH$_2$), 1.39 (s, 18H, C[CH$_3$]$_3$).

1,11-bis-{3-[1-(n-propyl)ureado]}-4,8-[N-(tertbutyl) oxycarbonyl)]-4,8-diazaundecane (43q)

Compound 43q was prepared from 291 mg of 41a (0.0008 mol) and n-propylisothiocyanate according to the procedure described above for 43e to afford 43q (359 mg, 91%) as viscous oil. Rf: 0.63 (CH$_2$Cl$_2$/MeOH/NH$_4$OH, 89:10:1). $^1$H NMR (CDCl$_3$): δ 5.60 (bs, 1H, NH), 4.70 (bs, 1H, NH), 3.05-3.28 (m, 16H, N—CH$_2$), 1.60-1.78 (m, 6H, CH$_2$CH$_2$), 1.47 (m, J=7.2, 4H, CH$_2$CH$_3$), 1.42 (s, 18H, C[CH$_3$]$_3$), 0.88 (t, J=7.2 Hz, 6H, CH$_2$CH$_3$).

1,11-bis-{3-[1-(3,3-diphenylpropyl)ureado]}-4,8-[N-(tertbutyl)oxycarbonyl)]-4,8-diazaundecane (43t)

Compound 43t was prepared from 194 mg (0.0005 mol) of 41a and 35c according to the procedure described above for 43e to afford 43t (420 mg, 98%) as a viscous oil. Rf: 0.58 (CH$_2$Cl$_2$/MeOH/NH$_4$OH, 89:10:1). $^1$H NMR (CDCl$_3$): δ 7.29-7.15 (m, 20H, Ar—H), 5.50 (b, 2H, NH), 3.96 (t, 2H, J=8.0 Hz, CHPh$_2$), 3.25 (t, 4H, J=6.4 Hz, NCH$_2$), 3.10 (b, 12H, NCH$_2$), 2.23 (q, 4H, J=7.2 Hz, NCH$_2$), 1.72 (b, 2H, CH$_2$CH$_2$), 1.61 (b, 4H, CH$_2$CH$_2$), 1.42 (s, 18H, C[CH$_3$]$_3$).

1,12-bis-{3-[1-(3,3-diphenylpropyl)ureado]}-4,9-[N-(tertbutyl)oxycarbonyl)]-4,9-diazadodecane (43v)

Compound 43v was prepared from 193 mg of 41b (0.0005 mol) and 35c according to the procedure described above for 43e to afford 43v (386 mg, 92%) as viscous oil. $^1$H NMR (CDCl$_3$): δ 7.29-7.13 (m, 22H, Ar—H, and NH), 5.50 (b, 2H, NH), 3.96 (t, 2H, J=8.0 Hz, CHPh$_2$), 3.25 (t, 4H, J=6.4 Hz, NCH$_2$), 3.10 (m, 12H, NCH$_2$), 2.24 (b, 4H, CH$_2$CH$_2$), 1.60 (b, 4H, CH$_2$CH$_2$), 1.42 (s, 22H, CH$_2$CH$_2$ and C[CH$_3$]$_3$).

1,15-bis-{3-[1-(3,3-diphenylpropyl)ureado]}-4,12-[N-(tertbutyl)oxycarbonyl)]-4,12-diazapentadecane (43x)

Compound 43x was prepared from 158 mg of 41c (0.0004 mol) and 35c according to the procedure described above for 43e to afford 43x (310 mg, 95%) as viscous oil; Rf: 0.50 (CH$_2$Cl$_2$/MeOH/NH$_4$OH, 89:10:1). $^1$H NMR (CDCl$_3$): δ 7.30-7.12 (m, 20H, Ar—H), 5.50 (b, 2H, NH), 4.40 (b, 2H, NH), 3.97 (t, 2H, J=7.2 Hz, CHPh$_2$), 3.25 (t, 4H, J=6.4 Hz, NCH$_2$), 3.10 (bs, 12H, NCH$_2$), 2.26 (q, 4H, J=8.0 Hz, CH$_2$CH$_2$), 1.60 (bs, 4H, CH$_2$CH$_2$), 1.42 ((s, 18H, C[CH$_3$]$_3$), 1.24 (bs, 6H, CH$_2$CH$_2$).

Example 5

General Procedure for Preparation of N-Boc Protected (bis)carbamylureas 51-53

1,12-bis-{5-[1-(N,N-diphenyl)carbamyl]ureado}-4,9-[N-(tertbutyl)oxycarbonyl)]-4,9-diazadodecane (51)

A 0.34 g portion of N,N-diphenylamine 48 (0.34 g, 0.0002 mol) in 5 mL of dry CH$_2$Cl$_2$ was added dropwise into a cold solution of N-chlorocarbonylisocyanate 45 (0.22 g, 0.0002 mol) in 5.0 mL of CH$_2$Cl$_2$, and the reaction was stirred for 30 min under N$_2$ atmosphere. A solution of 41b (0.3 g, 0.0008 mol) and NEt$_3$ (0.3 g, 0.0003 mol) in 10 mL of CH$_2$Cl$_2$ was then added via syringe, and the reaction mixture was allowed to stir at room temperature for 18 h. During this time, the progress for formation of product was monitored by TLC(CH$_2$Cl$_2$/MeOH/NH$_4$OH, 89:10:1). The dichloromethane was removed under reduced pressure to produce a viscous material, which was purified by flash chromatography on silica gel eluted with CH$_2$Cl$_2$/MeOH/NH$_4$OH (89:10:1) to furnish pure 51 as a white solid (140 mg, 21%). $^1$H NMR (CDCl$_3$): δ 8.44 (s, 2H, NH), 7.41-7.39 (m, 8H, Ar—H), 7.29-7.23 (m, 12H, Ar—H), 6.75 (s, 2H, NH), 3.25-3.08 (m, 12H, NCH$_2$), 1.78-1.69 (m, 6H, CH$_2$CH$_2$), 1.43 (s, 18H, C[CH$_3$]$_3$).

1,15-bis-{5-[1-(N,N-diphenyl)carbamyl]ureado}-4,12-[N-(tertbutyl)oxycarbonyl)]-4,12-diazapentadecane (52)

Compound 52 was made from 48, 45 and 41c according to the procedure described above for the synthesis of 51 to afford pure 52 (140 mg, 21%) as a viscous material. Rf: 0.88 (CH$_2$Cl$_2$/MeOH/NH$_4$OH 89:10:1). $^1$H NMR (CDCl$_3$): δ 8.40 (s, 2H, NH), 7.37-7.28 (m, 8H, Ar—H), 7.20-7.12 (m, 12H, Ar—H), 6.76 (s, 2H, NH), 3.23-3.06 (m, 12H, NCH$_2$), 1.72 (m, 4H, CH$_2$CH$_2$), 1.39 (bs, 22H, CH$_2$CH$_2$ and C[CH$_3$]$_3$). HRMS (CSI-MS m/z) calcd for C$_{48}$H$_{62}$N$_8$O$_8$ [M$^+$]=878.47; found 879.40 [M$^+$H].

1,11-bis-{5-[1-(N,N-diphenyl)carbamyl]ureado}-4,8-[N-(tertbutyl)oxycarbonyl)]-4,8-diazaundecane (53)

Compound 55 was made from 48, 45 and 41a according to the procedure described above for the synthesis of 51 to afford pure 53 (115 mg, 18%) as a white solid. Rf: 0.90 (CH$_2$Cl$_2$/MeOH/NH$_4$OH, 89:10:1); $^1$H NMR (CDCl$_3$): δ 8.44 (s, 2H, NH), 7.41-7.37 (m, 8H, Ar—H), 7.31-7.27 (m, 12H, Ar—H), 6.77 (s, 2H, NH), 3.30-3.12 (m, 12H, NCH$_2$), 1.75 (t, 4H, J=6.8 Hz, CH$_2$CH$_2$), 1.47 (b, 4H, CH$_2$CH$_2$), 1.43 (s, 18H, C[CH$_3$]$_3$), 1.27 (b, 6H, CH$_2$CH$_2$).

Example 6

General Procedure for Cleavage of N-Boc Protecting Group 1,12-bis-{3-[1-(benzyl)thioureado]}-4,9-diazadodecane (3)

In a 100 mL round-bottom flask, a 0.4 g portion of 43d (402 mg, 0.0006 mol) was dissolved in 30 mL of HPLC grade EtOAc under a nitrogen atmosphere, and 4.0 mL of a 1.0 M solution of HCl in EtOAc was added. The reaction mixture was allowed to stir at room temperature for 48 h, during which time the formation of product was monitored by TLC(CH$_2$Cl$_2$/MeOH/NH$_4$OH 89:10:1 or 78:20:2). The product precipitated as a white crystalline solid during the course of the reaction. When completion of the reaction was confirmed by TLC, the solvent was removed under reduced pressure to produce a white powder. The solid product was stirred with 30 mL of fresh EtOAc, and the solvent was decanted. The solid so obtained was vacuum dried to give pure 3 as a white solid (315 mg, 95% yield). An analytical sample was obtained by purification on silica gel (CH$_2$Cl$_2$: MeOH:NH$_4$OH 89:10:1). $^1$H NMR (CD$_3$OD): δ 7.32-7.10 (m, 10H, Ar—H), 4.67 (s, 4H, CH$_2$Ph), 3.71 (t, 4H, J=5.6 Hz, NCH$_2$), 3.01 (bs, 8H, NCH$_2$), 1.95 (m, 4H, CH$_2$CH$_2$), 1.78 (bs, 4H, CH$_2$CH$_2$). MS (CI m/z) calcd for C$_{26}$H$_{40}$N$_6$S$_2$ [M$^+$.]=500.28; found 501.4 [M$^+$H].

1,12-bis-{3-[1-(benzyl)ureado]}-4,9-diazadodecane (4)

Compound 4 was prepared from 480 mg (0.0007 mol) of 43e according to procedure described above for the synthesis of 3 to afford 370 mg (94%) of 4 as a white solid; $^1$H NMR (D$_2$O): δ 7.32 (m, 4H, Ar—H), 7.26 (m, 6H, Ar—H), 4.22 (s, 4H, CH$_2$Ph), 3.16 (t, 4H, J=6.4 Hz, NCH$_2$), 2.88 (t, 4H, J=7.2 Hz, NCH$_2$), 2.81 (bs, 4H, NCH$_2$), 1.25 (p, 4H, J=6.4 and 7.2 Hz, CH$_2$CH$_2$), 1.57 (m, 4H, CH$_2$CH$_2$). $^{13}$C NMR (D$_2$O): δ 160.89 (C=O), 139.83, 129.00, 127.45, 126.97 (Ar—C), 46.96, 45.12, 43.66, 36.44, 26.71, 22.92 (CH$_2$).

1,12-bis-{3-[1-(ethyl)ureado]}-4,9-diazadodecane (5)

Compound 5 was prepared from 448 mg (0.0008 mol) of 43f according to procedure described above for the synthesis of 3 to afford 330 mg (96%) of 5 as a white solid. $^1$H NMR (D$_2$O): δ 3.15 (t, 4H, J=5.6 Hz, N—CH$_2$), 3.05-2.98 (m, 12H, NCH$_2$), 1.79 (p, 4H, J=7.2 Hz, CH$_2$CH$_2$), 1.71 (bs, 4H, CH$_2$CH$_2$), 1.01 (t, 6H, J=7.2 Hz, CH$_3$). $^{13}$C NMR (D$_2$O): δ 160.88 (C=O), 47.06, 45.31, 36.67, 35.27, 26.70, 23.06 (CH$_2$), 14.63 (CH$_3$).

1,12-bis-{3-[1-(ethyl)thioureado]}-4,9-diazadodecane (6)

Compound 6 was prepared from 470 mg (0.0008 mol) of 43g according to procedure described above for the synthesis of 3 to afford 314 mg (87%) of 6 as a white solid. $^1$H NMR (D$_2$O): δ 3.51 (bs, 4H, NCH$_2$), 3.31 (bs, 4H, NCH$_2$), 3.06 (bs, 4H, NCH$_2$), 1.93 (p, 4H, J=6.4 Hz, CH$_2$CH$_2$), 1.75 (bs, 4H, CH$_2$CH$_2$), 1.12 (t, 6H, J=6.0 Hz, CH$_3$). $^{13}$C NMR (DMSO-d$_6$): δ 154.38, 153.98 (C=O), 47.13, 45.00, 40.92, 26.13, 23.15 (CH$_2$), 13.49 (CH$_3$).

1,15-bis-{3-[1-(benzyl)ureado]}-4,12-diazapentadecane (7)

Compound 7 was prepared from 320 mg (0.0005 mol) of 43h according to procedure described above for the synthesis of 3 to afford 250 mg (95%) of 7 as a white solid. $^1$H NMR (D$_2$O): δ 7.35 (m, 4H, Ar—H), 7.28 (m, 6H, Ar—H), 4.25 (s, 4H, CH$_2$Ph), 3.18 (t, 4H, J=5.6 Hz, NCH$_2$), 2.88 (t, 4H, J=7.2 Hz, NCH$_2$), 2.81 (t, 4H, J=8.0 Hz, NCH$_2$), 1.76 (p, 4H, J=7.2 Hz, CH$_2$CH$_2$), 1.53 (m, 4H, CH$_2$CH$_2$), 1.26 (bs, 6H, CH$_2$CH$_2$). $^{13}$C NMR (D$_2$O): δ 160.91 (C=O), 139.83, 129.01, 127.48, 126.99 (Ar—C), 47.78, 44.97, 43.68, 36.47, 27.87, 26.71, 25.64, 25.59 (CH$_2$).

1,12-bis-{3-[1-(n-propyl)ureado]}-4,9-diazadodecane (8)

Compound 8 was prepared from 330 mg (0.0006 mol) of 43i according to procedure described above for the synthesis of 3 to afford 228 mg (90%) of 8 as a white solid. $^1$H NMR (D$_2$O): δ 3.14 (t, 4H, J=6.4 Hz, NCH$_2$), 3.00-2.95 (m, 12H, NCH$_2$), 1.79 (p, 4H, J=6.4 Hz, CH$_2$CH$_2$), 1.70 (bs, 4H, CH$_2$CH$_2$), 1.40 (q, 4H, J=6.4 Hz, CH$_2$CH$_2$), 0.79 (t, 6H, J=7.2 Hz, CH$_3$). $^{13}$C NMR (D$_2$O): δ 160.98 (C=O), 47.05, 45.31, 42.03, 36.67, 26.70, 23.05, 22.82 (CH$_2$), 10.77 (CH$_3$).

1,12-bis-{3-[1-(n-propyl)thioureado]}-4,9-diazadodecane (9)

Compound 9 was prepared from 350 mg (0.0006 mol) of 43j according to procedure described above for the synthesis of 3 to afford 240 mg (86%) of 9 as a white solid. $^1$H NMR (D$_2$O): δ 3.59 (b, 4H, NCH$_2$), 3.23 (b, 4H, NCH$_2$), 3.07-3.00 (m, 8H, NCH$_2$), 1.92 (p, 4H, J=7.2 and 6.4 Hz, CH$_2$CH$_2$), 1.75 (b, 4H, CH$_2$CH$_2$), 1.57-1.48 (m, 4H, CH$_2$CH$_2$), 0.85 (t, 6H, J=7.2 Hz, CH$_3$).

1,15-bis-{3-[1-(benzyl)thioureado]}-4,12-diazapentadecane (10)

Compound 10 was prepared from 340 mg (0.0005 mol) of 43k according to procedure described above for the synthesis of 3 to afford 214 mg (77%) of 10 as a white solid. $^1$H NMR (D$_2$O): δ 7.37-7.30 (m, 10H, Ar—H), 4.58 (b, 4H, CH$_2$Ph), 3.58 (b, 4H, NCH$_2$), 3.10-2.80 (m, 8H, NCH$_2$), 1.85 (b, 4H, CH$_2$CH$_2$), 1.59 (b, 4H, CH$_2$CH$_2$), 1.32 (b, 6H, CH$_2$CH$_2$).

1,15-bis-{3-[1-(ethyl)ureado]}-4,12-diazapentadecane (11)

Compound 11 was prepared from 255 mg (0.0004 mol) of 43l according to procedure described above for the synthesis of 3 to afford 178 mg (89%) of 11 as a white solid. $^1$H NMR (D$_2$O): δ 3.16 (t, 4H, J=7.2 Hz, NCH$_2$), 3.08 (q, 4H, J=7.6 Hz, NCH$_2$), 2.99 (m, 8H, NCH$_2$), 1.79 (p, 4H, J=7.2 Hz, CH$_2$CH$_2$), 1.62 (bs, 4H, CH$_2$CH$_2$), 1.32 (s, 6H, CH$_2$CH$_2$), 1.02 (t, 6H, J=7.2 Hz, CH$_3$). $^{13}$C NMR (D$_2$O): δ 160.92 (C=O), 47.079, 45.15, 36.67, 35.25, 27.89, 26.69, 25.66 (CH$_2$), 14.65 (CH$_3$).

1,15-bis-{3-[1-(n-propyl)ureado]}-4,12-diazapentadecane (12)

Compound 12 was prepared from 255 mg (0.0004 mol) of 43m according to procedure described above for the synthesis of 3 to afford 180 mg (89%) of 12 as a white solid. $^1$H NMR (D$_2$O): δ 3.16 (t, 4H, J=5.6 Hz, NCH$_2$), 2.99 (m, 12H, NCH$_2$), 1.79 (p, 4H, J=7.2 Hz, CH$_2$CH$_2$), 1.62 (m, 4H, CH$_2$CH$_2$), 1.42 (q, 4H, J=6.4 Hz, CH$_2$CH$_2$), 1.32 (bs, 6H, CH$_2$CH$_2$), 0.81 (t, 6H, J=7.2 Hz, CH$_3$);). $^{13}$C NMR (D$_2$O): δ 161.03 (C=O), 47.79, 45.14, 42.00, 36.67, 27.89, 26.71, 25.65, 22.86 (CH$_2$), 10.77 (CH$_3$).

1,11-bis-{3-[1-(benzyl)thioureado]}-4,8-diazaundecane (13)

Compound 13 was prepared from 373 mg (0.0005 mol) of 43n according to procedure described above for the synthesis of 3 to afford 302 mg (99%) of 13 as white solid. $^1$H NMR (DMSO-d$_6$): δ 9.09 (bs, 2H, NH), 8.21 (t, 2H, NH), 8.00 (bs, 2H, NH), 7.20-7.32 (m, 10H, Ar—H), 4.64 (bs, 4H, N—CH$_2$), 3.48 (bs, 4H, N—CH$_2$), 2.97 (bs, 4H, N—CH$_2$), 2.87 (bs, 4H, N—CH$_2$), 2.02 (p, 2H, CH$_2$CH$_2$), 1.86 (p, 4H, CH$_2$CH$_2$). $^{13}$C NMR (DMSO-d$_6$): δ 128.92, 127.91, 127.45 (Ar—C), 47.43, 45.30, 44.60, 41.33, 26.37, 23.01 (CH$_2$).

1,11-bis-{3-[1-(ethyl)ureado]}-4,8-diazaundecane (14)

Compound 14 was prepared from 245 mg (0.0005 mol) of 43o according to procedure described above for the synthesis of 3 to afford 178 mg (96%) of 14 as white solid. $^1$H NMR (DMSO-d$_6$): δ 9.14 (bs, 2H, NH), 6.00 (bs, 4H, NH), 2.88-3.08 (m, 12H, CH$_2$N), 2.82 (bs, 4H, CH$_2$N), 2.02 (bs, 2H, CH$_2$CH$_2$), 1.71 (bs, 4H, CH$_2$CH$_2$), 0.95 (t, J=7.2 Hz, 6H, CH$_2$CH$_3$). $^{13}$C NMR (DMSO-d$_6$): δ 159.16 (C=O), 45.25, 44.51, 36.84, 34.80, 27.51, 22.98 (CH$_2$), 16.34 (CH$_3$).

1,11-bis-{3-[1-(benzyl)ureado]}-4,8-diazaundecane (15)

Compound 15 was prepared from 485 mg (0.0007 mol) of 43p according to procedure described above for the synthesis of 3 to afford 364 mg (99%) of 15 as white solid. $^1$H NMR (DMSO-d$_6$): δ 9.21 (bs, 6H, NH), 7.17-7.30 (m, 10H, Ar—H), 4.19 (s, 4H, N—CH$_2$), 3.08 (bs, 4H, N—CH$_2$), 2.94 (bs, 2H, N—CH$_2$), 2.82 (bs, 4H, N—CH$_2$), 2.02 (b, 2H, CH$_2$CH$_2$), 1.74 (b, 4H, CH$_2$CH$_2$). $^{13}$C NMR (DMSO-d$_6$): δ 159.24 (C=O), 141.49, 128.89, 127.63, 127.20 (Ar—C), 45.27, 44.53, 43.57, 37.02, 27.45, 22.93 (CH$_2$).

1,11-bis-{3-[1-(n-propyl)ureado]}-4,8-diazaundecane (16)

Compound 16 was prepared from 359 mg (0.0006 mol) of 43q according to procedure described above for the synthesis of 3 to afford 303 mg (99%) of 16 as a white solid. $^1$H NMR (DMSO-d$_6$): δ 9.24 (bs, 6H, NH), 2.82-3.06 (m, 16H, N—CH$_2$), 2.04 (b, 2H, CH$_2$CH$_2$), 1.73 (b, 4H, CH$_2$CH$_2$), 1.33 (m, J=7.2 Hz, 4H, CH$_2$CH$_3$), 0.80 (t, J=7.2 Hz, 4H, CH$_2$CH$_3$). $^{13}$C NMR (DMSO-d$_6$): δ 159.29 (C=O), 45.22, 44.52, 41.88, 36.97, 27.39, 23.78, 22.92 (CH$_2$), 12.04 (CH$_3$).

1,11-bis-{3-[1-(n-propyl)ureado]}-4,8-diazaundecane (17)

Compound 17 was prepared from 379 mg (0.0006 mol) of 43r according to procedure described above for the synthesis of 3 to afford 317 mg (99%) of 17 as white solid. $^1$H NMR (DMSO-d$_6$): δ 9.46 (b, 2H, NH), 9.16 (b, 2H, NH), 7.82 (b, 2H, NH), 2.85-3.90 (b, 16H, N—CH$_2$), 1.84 (b, 2H, CH$_2$CH$_2$), 1.59 (b, 4H, CH$_2$CH$_2$), 1.44 (m, 4H, CH$_2$CH$_3$), 0.85 (t, 6H, CH$_2$CH$_3$). $^{13}$C NMR (DMSO-d$_6$): δ 45.30, 44.58, 26.37, 22.92, 22.71, 22.00 (CH$_2$), 12.10 (CH$_3$).

1,11-bis-{3-[1-(ethyl)thioureado]}-4,8-diazaundecane (18)

Compound 18 was prepared from 347 mg (0.0006 mol) of 43s according to procedure described above for the synthesis of 3 to afford 282 mg (99%) of 18 as white solid; $^1$H NMR (DMSO-d$_6$): δ 9.10 (bs, 2H, NH), 7.78 (bs, 2H, NH), 7.70 (bs, 2H, NH), 3.43 (bs, 4H, N—CH$_2$), 3.32 (bs, 4H, N—CH$_2$), 2.97 (bs, 4H, N—CH$_2$), 2.86 (bs, 4H, N—CH$_2$), 2.02 (b, 2H, CH$_2$CH$_2$), 1.83 (b, 4H, CH$_2$CH$_2$), 1.02 (t, J=7.2 Hz, 6H, CH$_2$CH$_3$); $^{13}$C NMR (DMSO-d$_6$): δ 45.27, 44.58, 38.83, 31.99, 26.38, 22.98 (CH$_2$), 15.12 (CH$_3$).

1,11-bis-{3-[1-(3,3-diphenylpropyl)ureado]}-4,8-diazaundecane (19)

Compound 19 was prepared from 400 mg (0.0005 mol) of 43t according to procedure described above for the synthesis of 3 to afford 290 mg (86%) of 19 as a white solid. $^1$H NMR (DMSO-d$_6$): δ 9.10 (bs, 4H, NH), 7.27-7.21 (m, 16H, Ar—H), 7.18-7.10 (m, 4H, Ar—H), 3.96 (t, 2H, J=7.2 Hz, CHPh$_2$), 3.02 (t, 4H, J=6.4 Hz, NCH$_2$), 2.92 (b, 4H, NCH$_2$), 2.84 (t, 4H, J=7.2 Hz, NCH$_2$), 2.79 (bs, 4H, NCH$_2$), 2.09 (q, 4H, J=8.0 Hz, CH$_2$CH$_2$), 1.99 (m, 2H, CH$_2$CH$_2$), 1.69 (m, 4H, CH$_2$CH$_2$). $^{13}$C NMR (DMSO-d$_6$): δ 159.22 (CO), 145.50, 129.08, 128.28, 126.72 (Ar—C), 48.51, 45.25, 44.49, 38.77, 36.88, 36.07, 27.45, 22.95 (CH and CH$_2$).

1,11-bis-{3-[1-(3,3-diphenylpropyl)thioureado]}-4,8-diazaundecane (20)

Compound 20 was prepared from 260 mg (0.0003 mol) of 43u according to procedure described above for the synthesis of 3 to afford 205 mg (92%) of 20 as a white solid. $^1$H NMR (DMSO-d$_6$): δ 9.10 (b, 4H, NH), 7.91 (b, 2H, NH), 7.32-7.14 (m, 20H, Ar—H), 6.10 (b, 2H, NH), 4.04 (t, 2H, J=7.6 Hz, CHPh$_2$), 3.45 (b, 4H, NCH$_2$), 3.24 (b, 4H, NCH$_2$), 2.98 (b, 4H, NCH$_2$), 2.88 (b, 4H, NCH$_2$), 2.61 (m, 4H, CH$_2$CH$_2$), 2.04 (m, 2H, CH$_2$CH$_2$), 1.85 (m, 4H, CH$_2$CH$_2$); $^{13}$C NMR (DMSO-d$_6$): δ 145.36, 129.11, 128.31, 126.78 (Ar—C), 48.62, 45.29, 44.60, 42.80, 41.02, 34.97, 26.34, 22.96 (CH and CH$_2$).

1,12-bis-{3-[1-(3,3-diphenylpropyl)ureado]}-4,9-diazadodecane (21)

Compound 21 was prepared from 370 mg (0.42 mmol) of 43v according to procedure described above for the synthesis of 3 to afford 285 mg (90%) of 21 as a white solid; $^1$H NMR (DMSO-d$_6$): δ 9.00 (bs, 4H, NH), 7.21-7.12 (m, 20H, Ar—H, and NH), 3.96 (t, 2H, J=7.2 Hz, CHPh$_2$), 3.02 (t, 4H, J=6.4 Hz, NCH$_2$), 2.84 (t, 4H, J=6.4 Hz, NCH$_2$), 2.79 (b, 12H, NCH$_2$), 2.09 (q, 4H, J=7.2 Hz, CH$_2$CH$_2$), 1.69 (t, 4H, J=6.4 Hz, CH$_2$CH$_2$), 1.63 (b, 4H, CH$_2$CH$_2$); $^{13}$C NMR (DMSO-d$_6$): δ 159.27 (C=O), 145.49, 129.08, 128.28, 126.73 (Ar—C), 48.49, 46.50, 45.10, 38.76, 36.88, 36.07, 27.46, 23.23 (CH and CH$_2$). MS (EI m/z) calculated for C$_{42}$H$_{56}$N$_6$O$_2$ [M$^+$.]=676.45; found 677.40 [M$^+$H].

1,12-bis-{3-[1-(3,3-diphenylpropyl)thioureado]}-4,9-diazadodecane (22)

Compound 22 was prepared from 260 mg (0.0003 mol) of 43w according to procedure described above for the synthesis of 3 to afford 205 mg (92%) of 22 as a white solid. $^1$H NMR (DMSO-d$_6$): δ 9.02 (bs, 4H, NH), 8.02 (b, 2H, NH), 7.30-7.12 (m, 22H, Ar—H, and NH), 4.03 (t, 2H, J=7.6 Hz, CHPh$_2$), 3.43 (bs, 4H, NCH$_2$), 3.23 (bs, 4H, NCH$_2$), 2.85 (b, 8H, NCH$_2$), 2.24 (m, 4H, CH$_2$CH$_2$), 1.84 (b, 4H, CH$_2$CH$_2$), 1.67 (b, 4H, CH$_2$CH$_2$). $^{13}$C NMR (DMSO-d$_6$): δ 145.34, 129.14, 128.31, 126.79 (Ar—C), 48.58, 46.59, 45.13, 41.18, 34.93, 26.29, 23.26 (CH and CH$_2$).

1,15-bis-{3-[1-(3,3-diphenylpropyl)ureado]}-4,12-diazapentadecane (23)

Compound 23 was prepared from 290 mg (0.0003 mol) of 43x according to procedure described above for the synthesis of 3 to afford 225 mg (88%) of 23 as a white solid. $^1$H NMR (DMSO-d$_6$): δ 8.94 (bs, 4H, NH), 7.27-7.21 (m, 16H, Ar—H), 7.13-7.10 (m, 4H, Ar—H), 3.96 (t, 2H, J=7.2 Hz, CHPh$_2$), 3.02 (t, 4H, J=6.9 Hz, NCH$_2$), 2.84 (t, 4H, J=7.2 Hz, NCH$_2$), 2.77 (bs, 8H, NCH$_2$), 2.09 (d, 4H, J=7.2 Hz, CH$_2$CH$_2$), 1.69 (t, 4H, J=6.4 Hz, CH$_2$CH$_2$), 1.56 (bs, 4H, CH$_2$CH$_2$), 1.21 (bs, 6H, CH$_2$CH$_2$). $^{13}$C NMR (DMSO-d$_6$): δ 159.35 (C=O), 145.49, 129.07, 128.28, 126.72 (Ar—C), 48.49, 47.24, 45.09, 38.75, 36.82, 36.07, 28.55, 27.48, 26.37, 25.91 (CH and CH$_2$).

1,15-bis-{3-[1-(3,3-diphenylpropyl)thioureado]}-4,12-diazapentadecane (24)

Compound 24 was prepared from 287 mg (0.0003 mol) of 43y according to procedure described above for the synthesis of 3 to afford 230 mg (92%) of 24 as a white solid. $^1$H NMR (DMSO-d$_6$): δ 8.87 (bs, 4H, NH), 7.89 (bs, 4H, NH), 7.32-7.25 (m, 16H, Ar—H), 7.18-7.14 (m, 4H, Ar—H), 4.10 (b, 2H, CHPh$_2$), 3.44 (b, 4H, NCH$_2$), 3.23 (b, 4H, NCH$_2$), 2.87 (m, 8H, NCH$_2$), 2.25 (d, 4H, J=7.6 Hz, CH$_2$CH$_2$), 1.83 (t, 4H, J=7.2 Hz, CH$_2$CH$_2$), 1.68 (m, 4H, CH$_2$CH$_2$), 1.28 (b, 6H, CH$_2$CH$_2$). $^{13}$C NMR (DMSO-d$_6$): δ 145.37, 129.11, 128.30, 126.70 (Ar—C), 48.61, 47.30, 45.15, 41.42, 34.93, 28.58, 26.41, 25.94 (CH and CH$_2$).

1,15-bis-{3-[1-(2,2-diphenylethyl)thioureado]}-4,12-diazapentadecane (25)

Compound 25 was prepared from 260 mg (0.0003 mol) of 43z according to procedure described above for the synthesis of 3 to afford 201 mg (90%) of 25 as a white solid. $^1$H NMR (DMSO-d$_6$): δ 8.91 (bs, 3H, NH), 7.70 (b, 1H, NH), 7.52 (b, 1H, NH), 7.26 (bs, 16H, Ar—H), 7.16 (bs, 4H, Ar—H), 4.36 (b, 2H, CHPh$_2$), 4.04 (b, 4H, NCH$_2$), 3.45 (b, 4H, NCH$_2$), 2.78 (b, 8H, NCH$_2$), 1.78 (b, 4H, CH$_2$CH$_2$), 1.58 (b, 4H, CH$_2$CH$_2$), 1.25 (b, 6H, CH$_2$CH$_2$). $^{13}$C NMR (DMSO-d$_6$): δ 181.50 (C=S), 143.36, 129.16, 128.62, 127.07 (Ar—C), 50.44, 48.78, 47.30, 45.09, 28.59, 26.40, 26.25, 25.91 (CH$_2$).

1,12-bis-{3-[1-(2,2-diphenylethyl)thioureado]}-4,9-diazadodecane (26)

Compound 26 was prepared from 280 mg (0.0003 mol) of 43aa according to procedure described above for the synthesis of 3 to afford 214 mg (89%) of 26 as a white solid. $^1$H NMR (DMSO-d$_6$): δ 9.05 (b, 4H, NH), 7.79 (b, 2H, NH), 7.53 (bs, 2H, NH), 7.28 (bs, 16H, Ar—H), 7.14 (m, 4H, Ar—H), 4.36 (bs, 2H, CHPh$_2$), 4.02 (bs, 4H, NCH$_2$), 3.42 (bs, 4H, NCH$_2$), 2.81 (b, 8H, NCH$_2$), 1.80 (bs, 4H, CH$_2$CH$_2$), 1.66 (bs, 4H, CH$_2$CH$_2$). $^{13}$C NMR (DMSO-d$_6$): δ 183.29 (C=S), 143.39, 129.16, 128.63, 127.07 (Ar—C), 50.46, 48.76, 46.57, 45.09, 41.21, 26.25, 23.16 (CH and CH$_2$).

1,11-bis-{3-[1-(2,2-diphenylethyl)thioureado]}-4,8-diazaundecane (27)

Compound 27 was prepared from 330 mg (0.0004 mol) of 43bb according to procedure described above for the synthesis of 3 to afford 220 mg (79%) of 27 as a white solid. $^1$H NMR (DMSO-d$_6$): δ 9.13 (b, 4H, NH), 7.77 (bs, 2H, NH), 7.50 (bs, 2H, NH), 7.27 (bs, 16H, Ar—H), 7.16 (bs, 4H, Ar—H), 4.35 (bs, 2H, CHPh$_2$), 4.04 (b, 4H, NCH$_2$), 3.66 (bs, 4H, NCH$_2$), 3.42 (bs, 4H, NCH$_2$), 2.94 (bs, 4H, NCH$_2$), 2.80 (bs, 4H, NCH$_2$), 2.01 (b, 2H, CH$_2$CH$_2$), 1.79 (bs, 4H, CH$_2$CH$_2$). $^{13}$C NMR (DMSO-d$_6$): δ 183.20 (C=S), 143.38, 129.17, 128.63, 127.07 (Ar—C), 50.45, 48.68, 46.24, 44.57, 41.05, 26.28, 22.98 (CH and CH$_2$).

1,11-bis-{3-[1-(1,1-diphenylmethyl)thioureado]}-4,8-diazaundecane (28)

Compound 28 was prepared from 335 mg (0.0004 mol) of 43 cc according to procedure described above for the synthesis of 3 to afford 227 mg (80%) of 28 as a white solid. $^1$H NMR (DMSO-d$_6$): δ 8.90 (b, 4H, NH), 8.29 (b, 2H, NH), 7.40-7.22 (m, 20H, Ar—H), 6.72 (b, 2H, CH), 4.56 (b, NH), 3.52 (b, 4H, NCH$_2$), 2.97 (m, 8H, NCH$_2$), 2.02 (b, 2H, CH$_2$), 1.87 (b, 4H, CH$_2$CH$_2$). $^{13}$C NMR (DMSO-d$_6$): δ 183.22 (C=S), 143.43, 129.08, 127.89, 127.56 (Ar—C), 61.28 (CH), 45.37, 44.59, 41.34, 26.33, 23.00 (CH$_2$).

1,12-bis-{3-[1-(1,1-diphenylmethyl)thioureado]}-4,9-diazadodecane (29)

Compound 29 was prepared from 354 mg (0.0004 mmol) of 43dd according to procedure described above for the synthesis of 3 to afford 262 mg (87%) of 29 as a white solid. $^1$H NMR (DMSO-d$_6$): δ 8.95 (b, 4H, NH), 8.30 (bs, 2H, NH), 7.30 (m, 20H, Ar—H), 6.72 (b, 2H, CHPh$_2$), 3.51 (b, 4H, NCH$_2$), 2.88 (b, 8H, NCH$_2$), 1.87 (b, 4H, CH$_2$CH$_2$), 1.66 (b, 4H, CH$_2$CH$_2$). $^{13}$C NMR (DMSO-d$_6$): δ 183.26 (C=S), 143.42, 129.08, 127.89, 127.57 (Ar—C), 61.30 (CH), 46.60, 45.22, 41.42, 26.38, 23.28 (CH$_2$).

1,15-bis-{3-[1-(1,1-diphenylmethyl)thioureado]}-4,12-diazapentadecane (30)

Compound 30 was prepared from 390 mg (0.0004 mol) of 43ee according to procedure described above for the synthesis of 3 to afford 298 mg (89%) of 30 as a white solid. $^1$H NMR (DMSO-d$_6$): δ 8.90 (b, 4H, NH), 8.35 (b, 2H, NH), 7.30 (bs, 20H, Ar—H), 6.73 (bs, 2H, CHPh$_2$), 3.51 (bs, 4H, NCH$_2$), 2.89 (bs, 4H, NCH$_2$), 2.81 (bs, 4H, NCH$_2$), 1.87 (bs, 4H, CH$_2$CH$_2$), 1.60 (bs, 4H, CH$_2$CH$_2$), 1.26 (b, 6H, CH$_2$CH$_2$). $^{13}$C NMR (DMSO-d$_6$): δ 183.29 (C=S), 143.45, 129.06, 127.89, 127.55 (Ar—C), 61.30 (CH), 47.32, 45.23, 41.42, 28.59, 26.41, 25.93 (CH$_2$).

1,12-bis-{5-[1-(N,N-diphenyl)carbamyl]ureado}-4,9-diazadodecane (31)

Compound 31 was prepared from 51 (130 mg, 0.0002 mol) according to procedure described above for the synthesis of 3 to afford 85 mg of 31 (75%) as a white solid. $^1$H NMR (DMSO-d$_6$): δ 9.08 (bs, 4H, NH), 8.31 (t, 2H, J=5.6 Hz, NH), 7.86 (s, 2H, NH), 7.41-7.37 (m, 8H, Ar—H), 7.30-7.26 (m, 12H, Ar—H), 3.21 (m, 4H, NCH$_2$), 2.84 (bs, 8H, NCH$_2$), 1.81 (m, 4H, CH$_2$CH$_2$), 1.67 (bs, 4H, CH$_2$CH$_2$). $^{13}$C NMR (DMSO-d$_6$): δ 154.36, 153.97 (C=O), 142.41, 130.19, 128.45, 127.77 (Ar—C), 46.52, 45.13, 37.08, 26.70, 23.26 (CH$_2$). MS (EI m/z) calcd for C$_{38}$H$_{46}$N$_8$O$_4$ [M$^+$.]= 678.36; found 679.32 [M$^+$H].

1,15-bis-{5-[1-(N,N-diphenyl)carbamyl]ureado}-4,12-diazapentadecane (32)

Compound 32 was prepared from 52 (90 mg, 0.0001 mol) according to procedure described above for the synthesis of 3 to afford 42 mg of 32 (55%) as a white solid. $^1$H NMR (DMSO-d$_6$): δ 8.92 (b, 4H, NH), 8.32 (bs, 2H, NH), 7.88 (bs, 2H, NH), 7.40-7.31 (m, 20H, Ar—H), 3.21 (bs, 4H, NCH$_2$), 2.83 (bs, 8H, NCH$_2$), 1.81 (bs, 4H, CH$_2$CH$_2$), 1.60 (bs, 4H, CH$_2$CH$_2$), 1.27 (bs, 6H, CH$_2$CH$_2$). $^{13}$C NMR (DMSO-d$_6$): δ 154.39, 154.00 (C=O), 142.42, 130.01, 128.44, 127.79 (Ar—C), 45.27, 45.15, 37.04, 28.60, 26.73, 26.42, 25.96 (CH$_2$).

1,11-bis-{5-[1-(N,N-diphenyl)carbamyl]ureado}-4,8-diazaundecane (33)

Compound 33 was prepared from 53 (110 mg, 0.0001 mol) according to procedure described above for the synthesis of 3 to afford 66 mg of 33 (75%) as a white solid. $^1$H NMR (DMSO-d$_6$): δ 9.14 (bs, 4H, NH), 8.32 (t, 2H, J=5.6 Hz, NH), 7.87 (s, 2H, NH), 7.42-7.38 (m, 8H, Ar—H), 7.31-7.27 (m, 12H, Ar—H), 3.20 (m, 4H, NCH$_2$), 2.97 (bs, 4H, NCH$_2$), 2.84 (bs, 4H, NCH$_2$), 2.02 (m, 2H, CH$_2$CH$_2$), 1.81 (m, 4H, CH$_2$CH$_2$); $^{13}$C NMR (DMSO-d$_6$): δ 154.38, 153.98 (C=O), 142.42, 130.21, 128.46, 127.79 (Ar—C), 45.29, 44.56, 37.04, 26.74, 23.03 (CH$_2$).

Example 7

Expression, Purification and Demethylase Assay of Recombinant Proteins

Full-length human LSD1 cDNA was subcloned into the pET15b bacterial expression vector (Novagen, Madison, Wis.) in frame with an N-terminal 6×HIS-tag and transformed into the BL$_{21}$(DE$_3$) strain of *Escherichia coli*. Following selection, expression and purification of recombinant LSD1 protein were performed as previously described. Briefly, expression of LSD1-HIS protein was induced by 1 mM IPTG for 6 h at 25° C. The HIS-tagged protein was purified using Ni-NTA affinity purification resin and column as recommended by the manufacturer (Qiagen, Valencia, Calif.). Bound protein was eluted by imidazole and the eluate was dialyzed in PBS at 4° C. Enzymatic activity of LSD1 was examined using luminol-dependent chemiluminescence to measure the production of $H_2O_2$, as previously described. In brief, LSD1 activity was assayed in 50 mM Tris, pH 8.5, 50 mM KCl, 5 mM MgCl, 5 nmol luminol, and 20 µg/ml horseradish peroxidase with the indicated concentrations of H3K4me2 (1-21 aa) peptide as substrate. The integral values were calibrated against standards containing known concentrations of $H_2O_2$, and the activities expressed as pmols $H_2O_2$/mg protein/min. Reaction mixtures were incubated with or without 5 µg purified LSD1 in 50 mM Tris, pH 8.5, 50 mM KCl, 5 mM MgCl, 0.5% BSA, and 5% glycerol for 3 hr at 37° C. This reaction mixture was analyzed by Western blotting using antibodies (Millipore) that specifically recognize the dimethyl group of H3K4.

Western Blotting.

Cytoplasmic and nuclear fractions were prepared for Western blot analysis using the NE-PER™ Nuclear and Cytoplasmic Extraction Kit (Pierce, Rockford, Ill.). Primary antibodies against H3K4me2 were from Millipore. The pCNA monoclonal antibody was purchased from Oncogene Research Products (Cambridge, Mass.). Dye-conjugated secondary antibodies were used for quantification of Western blot results using the Odyssey Infrared Detection system and software (LI-COR Biosciences, Lincoln, Nebr.).

RNA Isolation and qPCR.

RNA was extracted using TRIzol reagents (Invitrogen, Carlsbad, Calif.). First-strand cDNA was synthesized using SuperScript III reverse transcriptase with an oligo(dT) primer (Invitrogen). qPCR was performed using the following primers: SFRP2 sense, 5'AAG CCT GCA AAA ATA AAA ATG ATG; SFRP2 antisense, 5'TGT AAA TGG TCT TGC TCT TGG TCT (annealing at 57.4° C.); GATA4 sense, 5'GGC CGC CCG ACA CCC CAA TCT; GATA4 antisense, 5' ATA GTG ACC CGT CCC ATC TCG (annealing at 64° C.). qPCR was performed in a MyiQ single color real-time PCR machine (Bio-Rad, Hercules, Calif.) with GAPDH as an internal control.

Determination of Cell Viability.

Calu-6 human anaplastic non-small cell lung carcinoma cells were maintained in culture using RPMI medium plus 10% fetal bovine serum. For the (3-(4,5-dimethylthiazol-2-yl)-5-(3-carboxymethoxyphenyl)-2-(4-sulfophenyl)-2H-tetrazolium) (MTS) reduction assay, 4000 cells/well were seeded in 100 µl medium in a 96-well plate and the cells were allowed to attach at 37° C. in 5% $CO_2$ for one day. The medium was aspirated and cells were treated with 100 µl of fresh medium containing appropriate concentrations of each test compound. The cells were incubated for 4 days at 37° C. in 5% $CO_2$. After 4 days 20 µL of the MTS reagent solution (Promega CellTiter 96 Aqueous One Solution Cell Proliferation Assay) was added to the medium. The cells were incubated for another 2 hours at 37° C. under 5% $CO_2$ environment. Absorbance was measured at 490 nm on a microplate reader equipped with SOFTmax PRO 4.0 software to determine the cell viability.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Those skilled in the art will recognize, or be able to ascertain using no more than routine experimentation, many equivalents of the specific embodiments of the invention described herein. Such equivalents are intended with be encompassed by the following claims.

What is claimed is:

1. A compound of formula II-a, II-b, II-c, or II-d

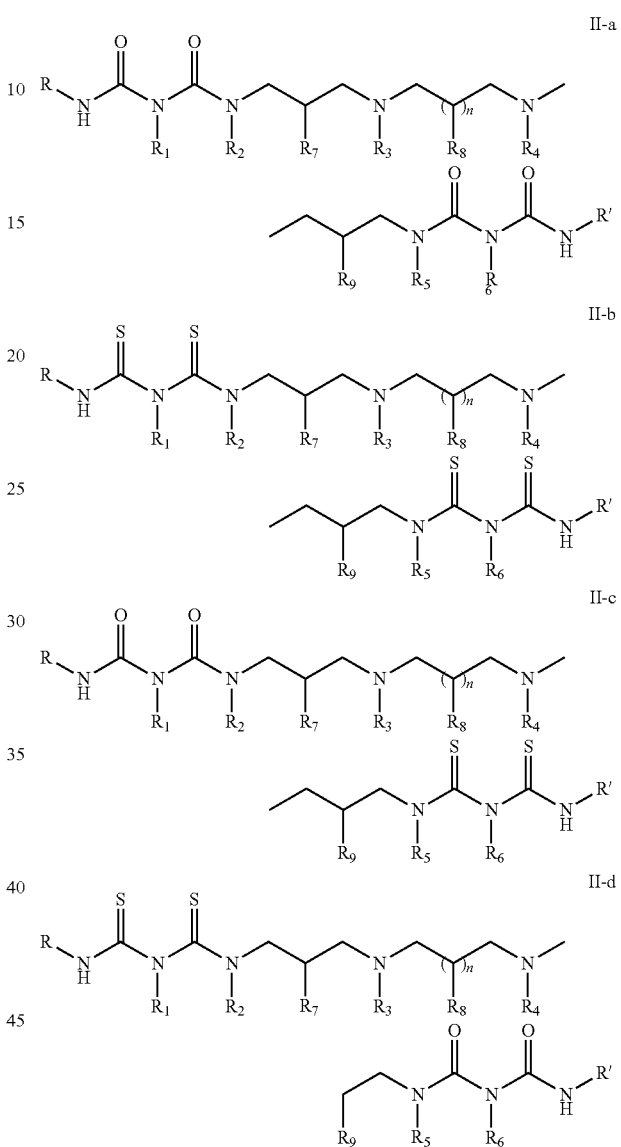

and salts, solvates and hydrates thereof, wherein, each R is independently H, —$C_1$-$C_8$ alkyl, —$C_6$-$C_{20}$ aralkyl, or —$C_3$-$C_{12}$ aryl; each of which is optionally substituted;

each R' is independently H, —$C_1$-$C_8$ alkyl, —$C_6$-$C_{20}$ aralkyl, or —$C_3$-$C_{12}$ aryl; each of which is optionally substituted;

each of $R_1$, $R_2$, $R_3$, $R_4$, $R_5$, and $R_6$ are independently selected from H, alkyl, aralkyl, haloalkyl, aryl, heteroaryl, and heteroaralkyl, each of which is optionally substituted;

each of $R_7$, $R_8$, and $R_9$ are independently selected from H, —$C_1$-$C_8$ alkyl, —$C_{2-8}$ alkenyl or —$C_2$-$C_8$ alkynyl, each containing 0, 1, 2, or 3 heteroatoms independently selected from O, S, and N; —$C_3$-$C_{12}$ cycloalkyl, —$C_3$-$C_{12}$ heterocycloalkyl, —$C_6$-$C_{20}$ aralkyl, —C$_3$-C$_{12}$ aryl, —C$_3$-C$_{12}$ heteroaryl, OR$_A$, SR$_A$, and NR$_A$R$_A$; each of which is optionally substituted;

each R$_A$ is independently selected from H, alkyl, aralkyl, aryl, or heteroaryl, each of which is optionally substituted; and n is 1, 2, 3, 4, 5, 6, 7, 8, 9, or 10.

2. The compound of claim 1, wherein each R is independently H, methyl, ethyl, propyl, i-propyl, butyl, s-butyl, t-butyl, pentyl, hexyl, heptyl, phenyl, benzyl, ethyl phenyl, propyl phenyl, or naphthyl, each of which is optionally substituted.

3. The compound of claim 1, wherein each R is independently H, methyl, ethyl, propyl, phenyl, benzyl, 3,3-diphenylpropyl, 2,2-diphenylethyl, or diphenylmethyl.

4. The compound of claim 1, wherein each R$_1$, R$_2$, R$_3$, R$_4$, R$_5$, and R$_6$ are H.

5. The compound of claim 1, wherein each R$_7$, R$_8$, and R$_9$ are H.

6. The compound of claim 1, wherein each n is independently 1, 2, 3, 4, 5, or 6.

7. A kit comprising an effective amount of a compound of claim 1 in unit dosage form, together with instructions for administering the compound to a subject suffering from or susceptible to a LSD1-related disease.

8. A compound selected from the group consisting of:

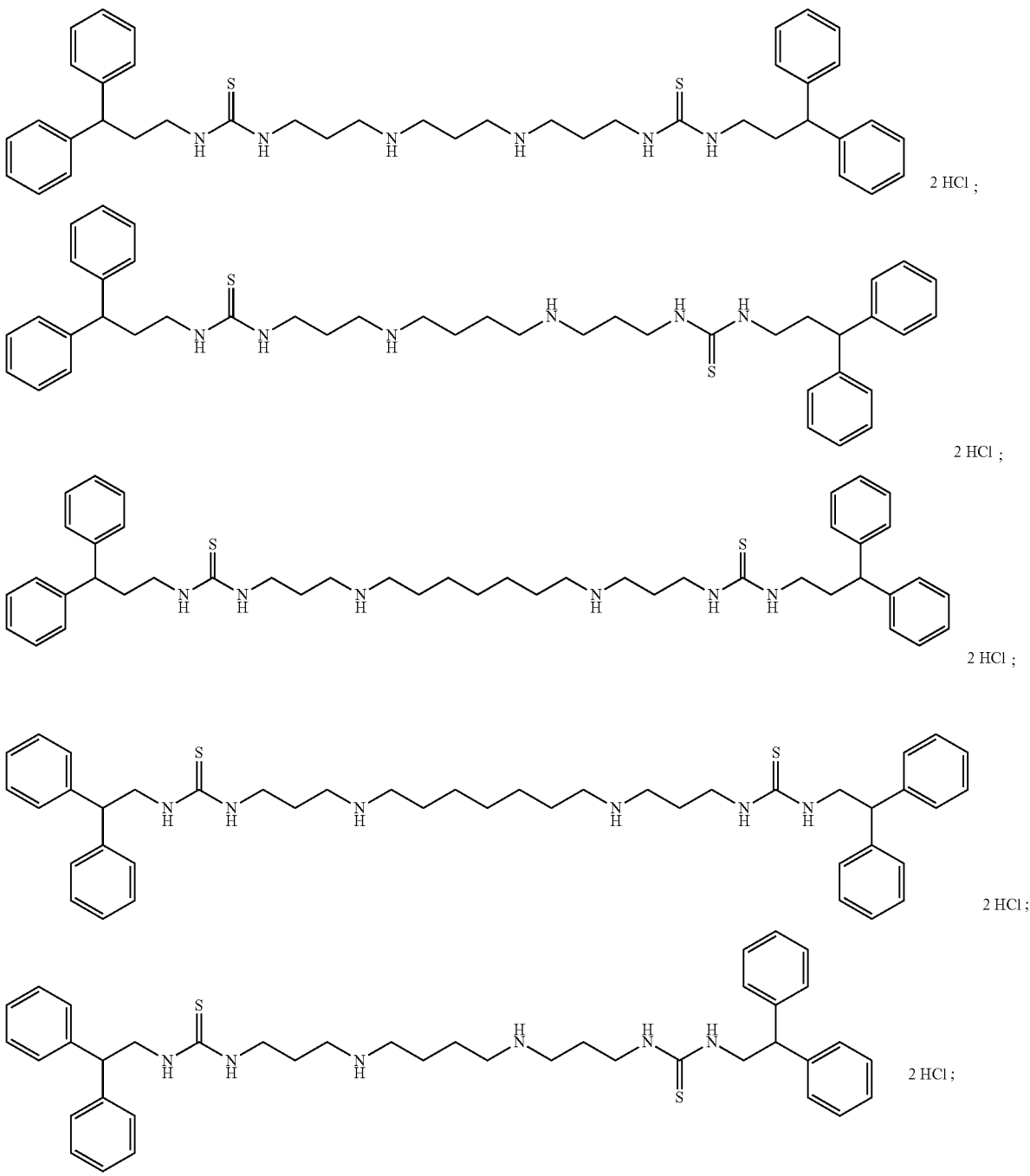

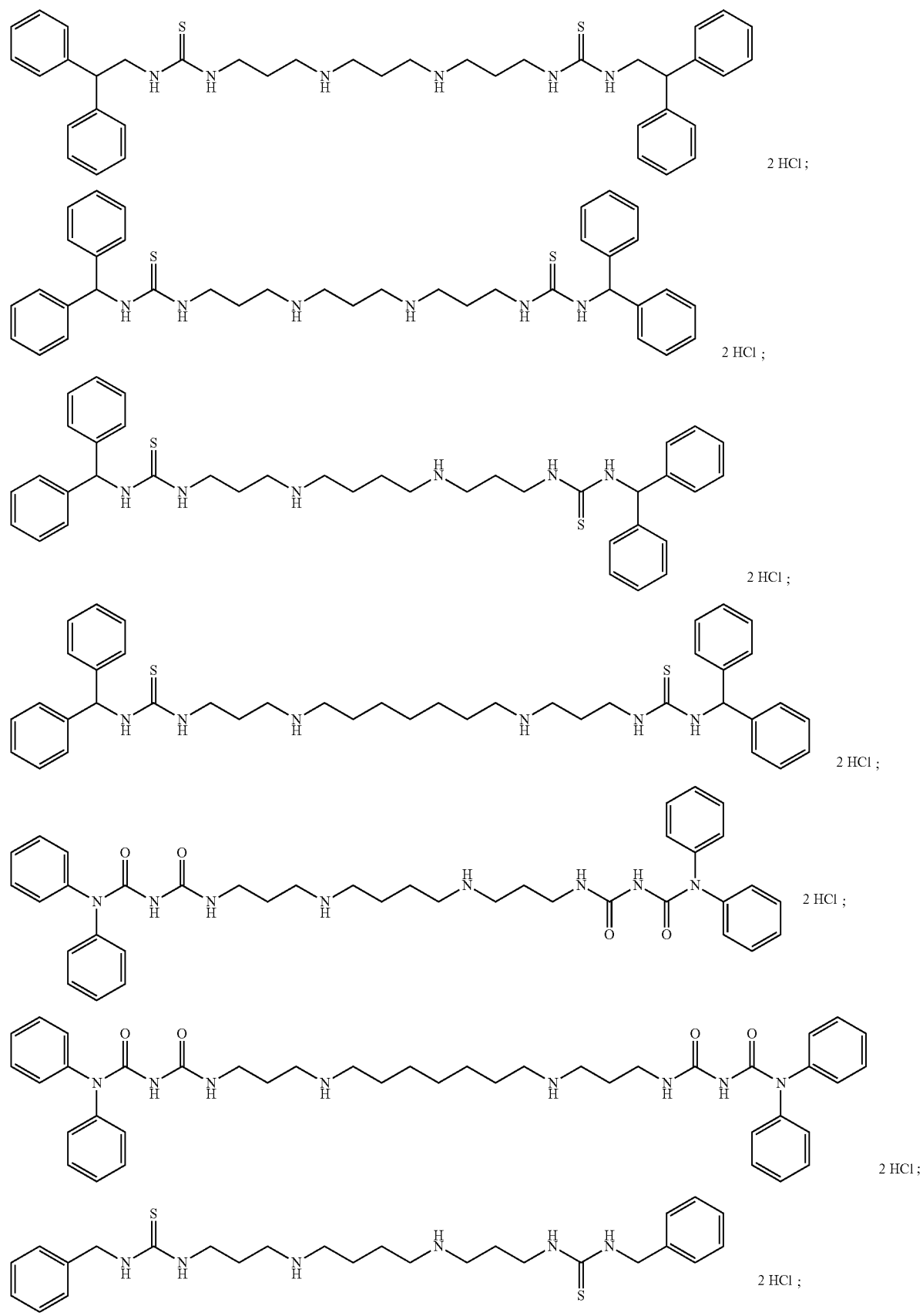

-continued
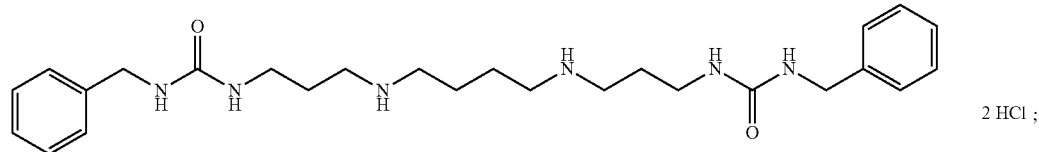
2 HCl;
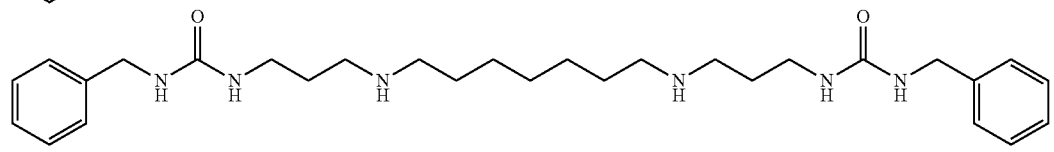
2 HCl;
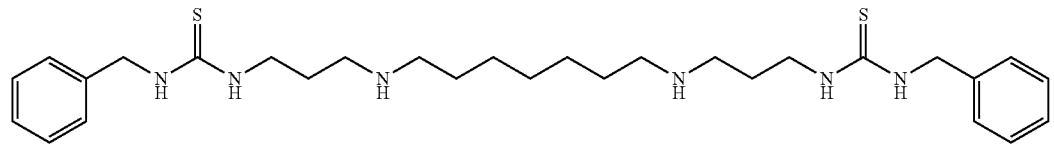
2 HCl;
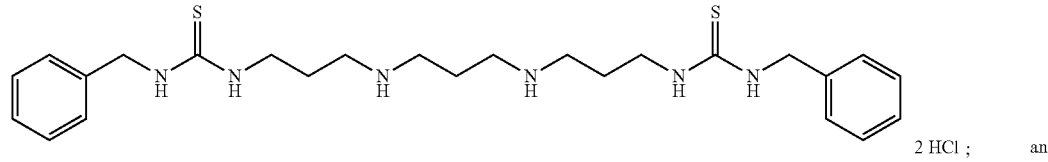
2 HCl; and
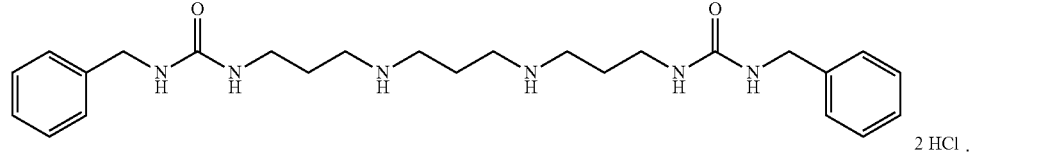
2 HCl.
* * * * *